(12) United States Patent
Murphy et al.

(10) Patent No.: US 8,071,112 B2
(45) Date of Patent: Dec. 6, 2011

(54) COMPOSITIONS AND METHODS OF USE OF ORF-1358 FROM BETA-HEMOLYTIC STREPTOCOCCAL STRAINS

(75) Inventors: Ellen Murphy, City Island, NY (US); Emily Mara Braunstein, New York, NY (US); Dorys Garcia-Hand, Croton-on-Hudson, NY (US); Annaliesa Sybil Anderson, Upper Saddle River, NJ (US); Ingrid Lea Dodge, Cornwall, NY (US); Eduardo Arturo Rojas, Briarcliff Manor, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 13/028,734

(22) Filed: Feb. 16, 2011

(65) Prior Publication Data

US 2011/0171263 A1    Jul. 14, 2011

Related U.S. Application Data

(62) Division of application No. 12/487,831, filed on Jun. 19, 2009, now Pat. No. 7,914,798.

(60) Provisional application No. 61/074,251, filed on Jun. 20, 2008.

(51) Int. Cl.
*A61K 39/09* (2006.01)

(52) U.S. Cl. ............... 424/244.1; 424/185.1; 424/190.1; 435/975; 530/350

(58) Field of Classification Search .................. None
See application file for complete search history.

(56) References Cited

FOREIGN PATENT DOCUMENTS

| WO | WO02/34771 A2 | 5/2002 |
|---|---|---|
| WO | WO02/083859 A2 | 10/2002 |
| WO | WO2005/076010 A2 | 8/2005 |
| WO | WO2006/042027 A2 | 4/2006 |

OTHER PUBLICATIONS

Banks DJ et al; J. Infect. Dis. 190:727-738 (2004).
Beres SB et al; Proc. Natl. Acad. Sci U.S.A. 103(18):7059-7064 (2006).
Efstratiou A; J of Medical Microbiology 29(3):207-220 (1989).
NCBI Genbank, zinc-binding adhesion liprotein [*Streptococcus agalactiae* 2603V/R], NP_687564.1 GI:22536713, accessed Aug. 19, 2010.
NCBI Genbank, High-affinity zinc uptake system protein znuA precursor[*Streptococcus pyogenes* MGAS10394], AAT86698.1, GI:50902983, accessed Aug. 19, 2010.
PCT International Search Report—Jan. 21, 2010.
Smoot JC et al; Proc. Natl. Acad. Sci. U.S.A. 99(7):4668-4673 (2002).
Sumby P. et al; J. Infect. Dis. 192:771-782 (2005).

*Primary Examiner* — Jennifer Graser
(74) *Attorney, Agent, or Firm* — Victoria S. Nolenda

(57) ABSTRACT

The present invention relates to polynucleotides encoding *Streptococcus* group C and G polypeptides and their use in immunogenic compositions. The invention also relates to immunogenic compositions comprising polypeptides encoded by those polynucleotides. In addition, the invention relates to methods of inducing an immune response in mammals against beta hemolytic *Streptococcus* or beta hemolytic *Streptococcus* infection using immunogenic compositions of the *Streptococcus* group C and G polypeptides and polynucleotides.

6 Claims, No Drawings

SEQUENCE LISTING

<160> NUMBER OF SEQ ID NOS: 32

<210> SEQ ID NO 1
<211> LENGTH: 1049
<212> TYPE: DNA
<213> ORGANISM: Streptococcus dysgalactiae

<400> SEQUENCE: 1

```
aaaaaaattc aagatgcaga tgcgttcgtt tatatggacg acaacatgga aacatggatt      60
tctgatgtta aaaaatcatt gaaatctaaa aaagtaacca ttgttaaagg aactggtaac     120
atgctacttg tagcaggagc tggacatgac catcaccatg aggatgctga caaaaagcat     180
gagcataata aacatagcga agaaggacac aaccatgctt ttgacccaca cgtgtggttg     240
tcaccatacc gtagcattac ggtcgttgaa atattcgcg acagtctttc aaaagcttac      300
ccagaaaaag cagagaactt caaagccaat gccgctactt atattgaaaa attaaaagag     360
cttgacaaag actatacggc agcactttca gatgctaagc aaaagagctt tgtcactcaa     420
catgctgctt ttggctacat ggcacttgac tatggcttga accaaatttc tattaatggt     480
gtcacaccag atgcagaacc atcagcaaaa cgtattgcta ctttgtcaaa atacgttaaa     540
aaatatggca tcaaatacat ttattttgag gaaatgctt caaataaggt agctaaaacg      600
ttagctaagg aagcaggagt taaaacagct gttcttagtc ctcttgaagg cttaacagaa     660
aaagaaatga agcaggcga agattacttt acagtcatgc gcaaaaacct tgaaacatta     720
cgcttgacga ctgatgttgc cggtaaagaa atccttccag aagaagatac cactaagaca     780
gtgtataatg gttacttcaa agataaagat gtcaaagacc gtaaattatc tgactggtct     840
ggtaactggc agtctgttta cccataccct caagatggca ctttagacca agtttgggat     900
tacaaggcta aaaatctaa aggtaaaatg acagcagctg aatacaaaga ttactacact      960
actggttaca aaactgatgt ggagcaaatc aacattaatg gtaagaaaaa caccatgaca    1020
tttgtgcgaa atggtgaaaa gaaaacctt                                     1049
```

<210> SEQ ID NO 2
<211> LENGTH: 349
<212> TYPE: PRT
<213> ORGANISM: Streptococcus dysgalactiae

<400> SEQUENCE: 2

```
Lys Lys Ile Gln Asp Ala Asp Ala Phe Val Tyr Met Asp Asp Asn Met
  1               5                  10                  15

Glu Thr Trp Ile Ser Asp Val Lys Lys Ser Leu Lys Ser Lys Lys Val
             20                  25                  30

Thr Ile Val Lys Gly Thr Gly Asn Met Leu Leu Val Ala Gly Ala Gly
             35                  40                  45

His Asp His His His Glu Asp Ala Asp Lys Lys His Glu His Asn Lys
 50                  55                  60

His Ser Glu Glu Gly His Asn His Ala Phe Asp Pro His Val Trp Leu
 65                  70                  75                  80

Ser Pro Tyr Arg Ser Ile Thr Val Val Glu Asn Ile Arg Asp Ser Leu
                 85                  90                  95

Ser Lys Ala Tyr Pro Glu Lys Ala Glu Asn Phe Lys Ala Asn Ala Ala
            100                 105                 110

Thr Tyr Ile Glu Lys Leu Lys Glu Leu Asp Lys Asp Tyr Thr Ala Ala
            115                 120                 125

Leu Ser Asp Ala Lys Gln Lys Ser Phe Val Thr Gln His Ala Ala Phe
130                 135                 140

Gly Tyr Met Ala Leu Asp Tyr Gly Leu Asn Gln Ile Ser Ile Asn Gly
145                 150                 155                 160

Val Thr Pro Asp Ala Glu Pro Ser Ala Lys Arg Ile Ala Thr Leu Ser
                165                 170                 175

Lys Tyr Val Lys Lys Tyr Gly Ile Lys Tyr Ile Tyr Phe Glu Glu Asn
            180                 185                 190

Ala Ser Asn Lys Val Ala Lys Thr Leu Ala Lys Glu Ala Gly Val Lys
            195                 200                 205

Thr Ala Val Leu Ser Pro Leu Glu Gly Leu Thr Glu Lys Glu Met Lys
210                 215                 220

Ala Gly Glu Asp Tyr Phe Thr Val Met Arg Lys Asn Leu Glu Thr Leu
225                 230                 235                 240

Arg Leu Thr Thr Asp Val Ala Gly Lys Glu Ile Leu Pro Glu Glu Asp
                245                 250                 255

Thr Thr Lys Thr Val Tyr Asn Gly Tyr Phe Lys Asp Lys Asp Val Lys
            260                 265                 270

Asp Arg Lys Leu Ser Asp Trp Ser Gly Asn Trp Gln Ser Val Tyr Pro
            275                 280                 285

Tyr Leu Gln Asp Gly Thr Leu Asp Gln Val Trp Asp Tyr Lys Ala Lys
290                 295                 300

Lys Ser Lys Gly Lys Met Thr Ala Ala Glu Tyr Lys Asp Tyr Tyr Thr
305                 310                 315                 320

Thr Gly Tyr Lys Thr Asp Val Glu Gln Ile Asn Ile Asn Gly Lys Lys
                325                 330                 335

Asn Thr Met Thr Phe Val Arg Asn Gly Glu Lys Lys Thr
            340                 345
```

<210> SEQ ID NO 3
<211> LENGTH: 1103
<212> TYPE: DNA
<213> ORGANISM: Streptococcus dysgalactiae

<400> SEQUENCE: 3

```
gattttgaac cgtcaaccaa agacattaaa aaaattcaag atgcagatgc gttcgtttat     60
atggacgaca acatggaaac atggatttct gatgttaaaa aatcattgac atctaaaaaa    120
gtaaccattg ttaaaggaac tggtaacatg ctacttgtag caggagctgg acatgaccat    180
```

-continued

```
caccatgagg atgctgacaa aaagcatgag cataataaac atagcgaaga aggacacaac    240
catgcttttg acccacacgt gtggttgtca ccataccgta gcattacggt cgttgaaaat    300
attcgcgaca gtctttcaaa agcttaccca gaaaagcag aaaacttcaa agccaatgcc     360
gctacttata ttgaaaaatt aaaagagctt gacaaagact atacggcagc actttcagat    420
gctaagcaaa agagctttgt cactcaacat gctgcttttg gctacatggc acttgactat    480
ggcttgaacc aaatttctat taatggtgtc acaccagata cagaaccatc agcaaaacgt    540
attgctactt tgtcaaaata cgttaaaaaa tatggcatca atacattta ttttgaggaa     600
aatgcttcaa ataaggtagc taaaacgtta gctaaggaag caggagttaa acagctgtt     660
cttagtccgc ttgaaggctt aacagaaaaa gaaatgaaag caggcgaaga ttactttaca    720
gtcatgcgca aaaaccttga acattacgc ttgacgactg atgttgccgg taaagaaatc     780
cttccagaag aagataccac taagacagtg tataatggtt acttcaaaga taaagatgtc    840
aaagaccgta attatctga ctggtctggt aactggcagt ctgtttaccc ataccttcaa     900
gatggcactt tagaccaagt ttgggattac aaggctaaaa atctaaagg taaaatgaca    960
gcagctgaat acaaagatta ctacactact ggttacaaaa ctgatgtgga gcaaatcaac   1020
attaatggta agaaaaacac catgacattt gtgcgaaatg gtgaaaagaa aacctttact   1080
tacaaatatg ctggtaaaga aat                                           1103
```

```
<210> SEQ ID NO 4
<211> LENGTH: 367
<212> TYPE: PRT
<213> ORGANISM: Streptococcus dysgalactiae

<400> SEQUENCE: 4
```

Asp Phe Glu Pro Ser Thr Lys Asp Ile Lys Lys Ile Gln Asp Ala Asp
1               5                   10                  15

Ala Phe Val Tyr Met Asp Asp Asn Met Glu Thr Trp Ile Ser Asp Val
            20                  25                  30

Lys Lys Ser Leu Thr Ser Lys Lys Val Thr Ile Val Lys Gly Thr Gly
        35                  40                  45

Asn Met Leu Leu Val Ala Gly Ala Gly His Asp His His Glu Asp
    50                  55                  60

Ala Asp Lys Lys His Glu His Asn Lys His Ser Glu Glu Gly His Asn
65                  70                  75                  80

His Ala Phe Asp Pro His Val Trp Leu Ser Pro Tyr Arg Ser Ile Thr
                85                  90                  95

Val Val Glu Asn Ile Arg Asp Ser Leu Ser Lys Ala Tyr Pro Glu Lys
            100                 105                 110

Ala Glu Asn Phe Lys Ala Asn Ala Thr Tyr Ile Glu Lys Leu Lys
        115                 120                 125

Glu Leu Asp Lys Asp Tyr Thr Ala Ala Leu Ser Asp Ala Lys Gln Lys
    130                 135                 140

Ser Phe Val Thr Gln His Ala Ala Phe Gly Tyr Met Ala Leu Asp Tyr
145                 150                 155                 160

Gly Leu Asn Gln Ile Ser Ile Asn Gly Val Thr Pro Asp Thr Glu Pro
                165                 170                 175

Ser Ala Lys Arg Ile Ala Thr Leu Ser Lys Tyr Val Lys Lys Tyr Gly
            180                 185                 190

Ile Lys Tyr Ile Tyr Phe Glu Glu Asn Ala Ser Asn Lys Val Ala Lys
        195                 200                 205

Thr Leu Ala Lys Glu Ala Gly Val Lys Thr Ala Val Leu Ser Pro Leu

```
                210                 215                 220
Glu Gly Leu Thr Glu Lys Glu Met Lys Ala Gly Glu Asp Tyr Phe Thr
225                 230                 235                 240

Val Met Arg Lys Asn Leu Glu Thr Leu Arg Leu Thr Thr Asp Val Ala
                245                 250                 255

Gly Lys Glu Ile Leu Pro Glu Glu Asp Thr Thr Lys Thr Val Tyr Asn
                260                 265                 270

Gly Tyr Phe Lys Asp Lys Asp Val Lys Asp Arg Lys Leu Ser Asp Trp
                275                 280                 285

Ser Gly Asn Trp Gln Ser Val Tyr Pro Tyr Leu Gln Asp Gly Thr Leu
                290                 295                 300

Asp Gln Val Trp Asp Tyr Lys Ala Lys Lys Ser Lys Gly Lys Met Thr
305                 310                 315                 320

Ala Ala Glu Tyr Lys Asp Tyr Tyr Thr Thr Gly Tyr Lys Thr Asp Val
                325                 330                 335

Glu Gln Ile Asn Ile Asn Gly Lys Lys Asn Thr Met Thr Phe Val Arg
                340                 345                 350

Asn Gly Glu Lys Lys Thr Phe Thr Tyr Lys Tyr Ala Gly Lys Glu
                355                 360                 365

<210> SEQ ID NO 5
<211> LENGTH: 881
<212> TYPE: DNA
<213> ORGANISM: Streptococcus intermedius

<400> SEQUENCE: 5
gaatctaaaa aagtaaccat tgttaaagga actggtaaca tgctacttgt agcaggagct      60
ggacatgacc atcaccatga ggatgctgac aaaaagcatg agcataataa acatagcgaa     120
gaaggacaca accatgcttt tgacccacac gtgtggttgt caccataccg tagcattacg     180
gtcgttgaaa atattcgcga cagtctttca aaagcttacc cagaaaaagc agagaacttc     240
aaagccaatg ccgctactta tattgaaaaa ttaaagagc ttgacaaaga ctatacggca     300
gcactttcag atgctaagca aaagagcttt gtcactcaac atgctgcttt tggctacatg     360
gcacttgact atggcttgaa ccaaatttct attaatggtg tcacaccaga tgcagaacca     420
tcagcaaaac gtattgctac tttgtcaaaa tacgttaaaa aatatggcat caaatacatt     480
tattttgagg aaaatgcttc aaataaggta gctaaacgt agctaaggaa gcaggagtt     540
aaaacagctg ttcttagtcc tcttgaaggc ttaacagaaa aagaaatgaa agcaggcgaa     600
gattacttta cagtcatgcg caaaaacctt gaaacattac gcttgacgac tgatgttgcc     660
ggtaaagaaa tccttccaga agaagatacc actaagacag tgtataatgg ttacttcaaa     720
gataaagatg tcaaagaccg taaattatct gactggtctg gtaactggca gtctgtttac     780
ccataccttc aagatggcac tttagaccaa gtttgggatt acaaggctaa aaaatctaaa     840
ggtaaaatga cagcagctga atacaaagat tactacacta c                        881

<210> SEQ ID NO 6
<211> LENGTH: 293
<212> TYPE: PRT
<213> ORGANISM: Streptococcus intermedius

<400> SEQUENCE: 6

Glu Ser Lys Lys Val Thr Ile Val Lys Gly Thr Gly Asn Met Leu Leu
1               5                  10                  15

Val Ala Gly Ala Gly His Asp His His Glu Asp Ala Asp Lys Lys
                20                  25                  30
```

His Glu His Asn Lys His Ser Glu Glu Gly His Asn His Ala Phe Asp
         35                  40                  45

Pro His Val Trp Leu Ser Pro Tyr Arg Ser Ile Thr Val Val Glu Asn
 50                  55                  60

Ile Arg Asp Ser Leu Ser Lys Ala Tyr Pro Lys Ala Glu Asn Phe
 65                  70                  75                  80

Lys Ala Asn Ala Ala Thr Tyr Ile Glu Lys Leu Lys Glu Leu Asp Lys
                 85                  90                  95

Asp Tyr Thr Ala Ala Leu Ser Asp Ala Lys Gln Lys Ser Phe Val Thr
             100                 105                 110

Gln His Ala Ala Phe Gly Tyr Met Ala Leu Asp Tyr Gly Leu Asn Gln
             115                 120                 125

Ile Ser Ile Asn Gly Val Thr Pro Asp Ala Glu Pro Ser Ala Lys Arg
 130                 135                 140

Ile Ala Thr Leu Ser Lys Tyr Val Lys Lys Tyr Gly Ile Lys Tyr Ile
145                 150                 155                 160

Tyr Phe Glu Glu Asn Ala Ser Asn Lys Val Ala Lys Thr Leu Ala Lys
                 165                 170                 175

Glu Ala Gly Val Lys Thr Ala Val Leu Ser Pro Leu Glu Gly Leu Thr
             180                 185                 190

Glu Lys Glu Met Lys Ala Gly Glu Asp Tyr Phe Thr Val Met Arg Lys
             195                 200                 205

Asn Leu Glu Thr Leu Arg Leu Thr Thr Asp Val Ala Gly Lys Glu Ile
 210                 215                 220

Leu Pro Glu Glu Asp Thr Thr Lys Thr Val Tyr Asn Gly Tyr Phe Lys
225                 230                 235                 240

Asp Lys Asp Val Lys Asp Arg Lys Leu Ser Asp Trp Ser Gly Asn Trp
                 245                 250                 255

Gln Ser Val Tyr Pro Tyr Leu Gln Asp Gly Thr Leu Asp Gln Val Trp
             260                 265                 270

Asp Tyr Lys Ala Lys Lys Ser Lys Gly Lys Met Thr Ala Ala Glu Tyr
             275                 280                 285

Lys Asp Tyr Tyr Thr
        290

<210> SEQ ID NO 7
<211> LENGTH: 852
<212> TYPE: DNA
<213> ORGANISM: Streptococcus constellatus subsp. constellatus

<400> SEQUENCE: 7
tctaaaaaag taaccattgt taaaggaact ggtaacatgc tacttgtagc aggagctgga       60
catgaccatc accatgagga tgctgacaaa aagcatgagc ataataaaca tagcgaagaa      120
ggacacaacc atgcttttga cccacacgtg tggttgtcac cataccgtag cattacggtc      180
gttgaaaata ttcgcgacag tctttcaaaa gcttacccag aaaaagcaga gaacttcaaa      240
gccaatgccg ctacttatat tgaaaaatta aaagagcttg acaaagacta tacggcagca      300
ctttcagatg ctaagcaaaa gagctttgtc actcaacatg ctgcttttgg ctacatggca      360
cttgactatg gcttgaacca aatttctatt aatggtgtca caccagatgc agaaccatca      420
gcaaaacgta ttgctacttt gtcaaaatac gttaaaaaat atggcatcaa atacatttat      480
tttgaggaaa atgcttcaaa taaggtagct aaaacgttag ctaaggaagc aggagttaaa      540
acagctgttc ttagtcctct tgaaggctta acagaaaaag aaatgaaagc aggcgaagat      600

```
tactttacag tcatgcgcaa aaaccttgaa acattacgct tgacgactga tgttgccggt    660
aaagaaatcc ttccagaaga agataccact aagacagtgt ataatggtta cttcaaagat    720
aaagatgtca agaccgtaa attatctgac tggtctggta actggcagtc tgtttaccca     780
taccttcaag atggcacttt agaccaagtt tgggattaca aggctaaaaa atctaaaggt    840
aaaatgacag ca                                                         852
```

```
<210> SEQ ID NO 8
<211> LENGTH: 284
<212> TYPE: PRT
<213> ORGANISM: Streptococcus constellatus subsp. constellatus

<400> SEQUENCE: 8

Ser Lys Lys Val Thr Ile Val Lys Gly Thr Gly Asn Met Leu Leu Val
1               5                   10                  15

Ala Gly Ala Gly His Asp His His Glu Asp Ala Asp Lys Lys His
            20                  25                  30

Glu His Asn Lys His Ser Glu Glu Gly His Asn His Ala Phe Asp Pro
        35                  40                  45

His Val Trp Leu Ser Pro Tyr Arg Ser Ile Thr Val Val Glu Asn Ile
    50                  55                  60

Arg Asp Ser Leu Ser Lys Ala Tyr Pro Glu Lys Ala Glu Asn Phe Lys
65                  70                  75                  80

Ala Asn Ala Ala Thr Tyr Ile Glu Lys Leu Lys Glu Leu Asp Lys Asp
                85                  90                  95

Tyr Thr Ala Ala Leu Ser Asp Ala Lys Gln Lys Ser Phe Val Thr Gln
            100                 105                 110

His Ala Ala Phe Gly Tyr Met Ala Leu Asp Tyr Gly Leu Asn Gln Ile
        115                 120                 125

Ser Ile Asn Gly Val Thr Pro Asp Ala Glu Pro Ser Ala Lys Arg Ile
    130                 135                 140

Ala Thr Leu Ser Lys Tyr Val Lys Lys Tyr Gly Ile Lys Tyr Ile Tyr
145                 150                 155                 160

Phe Glu Glu Asn Ala Ser Asn Lys Val Ala Lys Thr Leu Ala Lys Glu
                165                 170                 175

Ala Gly Val Lys Thr Ala Val Leu Ser Pro Leu Glu Gly Leu Thr Glu
            180                 185                 190

Lys Glu Met Lys Ala Gly Glu Asp Tyr Phe Thr Val Met Arg Lys Asn
        195                 200                 205

Leu Glu Thr Leu Arg Leu Thr Thr Asp Val Ala Gly Lys Glu Ile Leu
    210                 215                 220

Pro Glu Glu Asp Thr Thr Lys Thr Val Tyr Asn Gly Tyr Phe Lys Asp
225                 230                 235                 240

Lys Asp Val Lys Asp Arg Lys Leu Ser Asp Trp Ser Gly Asn Trp Gln
                245                 250                 255

Ser Val Tyr Pro Tyr Leu Gln Asp Gly Thr Leu Asp Gln Val Trp Asp
            260                 265                 270

Tyr Lys Ala Lys Lys Ser Lys Gly Lys Met Thr Ala
        275                 280

<210> SEQ ID NO 9
<211> LENGTH: 888
<212> TYPE: DNA
<213> ORGANISM: Streptococcus anginosus

<400> SEQUENCE: 9
```

```
ttgaaatcta aaaaagtaac cattgttaaa ggaactggta acatgctact tgtagcagga    60
gctggacatg accatcacca tgaggatgct gacaaaaagc atgagcataa taaacatagc   120
gaagaaggac acaaccatgc ttttgaccca cacgtgtggt tgtcaccata ccgtagcatt   180
acggtcgttg aaaatattcg cgacagtctt tcaaaagctt acccagaaaa agcagagaac   240
ttcaaagcca atgccgctac ttatattgaa aaattaaaag agcttgacaa agactatacg   300
gcagcacttt cagatgctaa gcaaaagagc tttgtcactc aacatgctgc ttttggctac   360
atggcacttg actatggctt gaaccaaatt tctattaatg gtgtcacacc agatgcagaa   420
ccatcagcaa aacgtattgc tactttgtca aaatacgtta aaaaatatgg catcaaatac   480
atttattttg aggaaaatgc ttcaaataag gtagctaaaa cgttagctaa ggaagcagga   540
gttaaaacag ctgttcttag tcctcttgaa ggcttaacag aaaaagaaat gaaagcaggc   600
gaagattact ttacagtcat gcgcaaaaac cttgaaacat acgcttgac gactgatgtt   660 gccggtaaag aaatccttcc agaagaagat accactaaga cagtgtataa tggttacttc   720
aaagataaag atgtcaaaga ccgtaaatta tctgactggt ctggtaactg gcagtctgtt   780
tacccatacc ttcaagatgg cactttagac caagtttggg attacaaggc taaaaaatct   840
aaaggtaaaa tgacagcagc tgaatacaaa gattactaca ctactggt                888
```

<210> SEQ ID NO 10
<211> LENGTH: 296
<212> TYPE: PRT
<213> ORGANISM: Streptococcus anginosus
<400> SEQUENCE: 10

```
Leu Lys Ser Lys Lys Val Thr Ile Val Lys Gly Thr Gly Asn Met Leu
1               5                   10                  15

Leu Val Ala Gly Ala Gly His Asp His His Glu Asp Ala Asp Lys
            20                  25                  30

Lys His Glu His Asn Lys His Ser Glu Glu Gly His Asn His Ala Phe
        35                  40                  45

Asp Pro His Val Trp Leu Ser Pro Tyr Arg Ser Ile Thr Val Val Glu
    50                  55                  60

Asn Ile Arg Asp Ser Leu Ser Lys Ala Tyr Pro Glu Lys Ala Glu Asn
65                  70                  75                  80

Phe Lys Ala Asn Ala Ala Thr Tyr Ile Glu Lys Leu Lys Glu Leu Asp
                85                  90                  95

Lys Asp Tyr Thr Ala Ala Leu Ser Asp Ala Lys Gln Lys Ser Phe Val
            100                 105                 110

Thr Gln His Ala Ala Phe Gly Tyr Met Ala Leu Asp Tyr Gly Leu Asn
        115                 120                 125

Gln Ile Ser Ile Asn Gly Val Thr Pro Asp Ala Glu Pro Ser Ala Lys
    130                 135                 140

Arg Ile Ala Thr Leu Ser Lys Tyr Val Lys Lys Tyr Gly Ile Lys Tyr
145                 150                 155                 160

Ile Tyr Phe Glu Glu Asn Ala Ser Asn Lys Val Ala Lys Thr Leu Ala
                165                 170                 175

Lys Glu Ala Gly Val Lys Thr Ala Val Leu Ser Pro Leu Glu Gly Leu
            180                 185                 190

Thr Glu Lys Glu Met Lys Ala Gly Glu Asp Tyr Phe Thr Val Met Arg
        195                 200                 205

Lys Asn Leu Glu Thr Leu Arg Leu Thr Thr Asp Val Ala Gly Lys Glu
    210                 215                 220
```

```
Ile Leu Pro Glu Glu Asp Thr Thr Lys Thr Val Tyr Asn Gly Tyr Phe
225                 230                 235                 240

Lys Asp Lys Asp Val Lys Asp Arg Lys Leu Ser Asp Trp Ser Gly Asn
                245                 250                 255

Trp Gln Ser Val Tyr Pro Tyr Leu Gln Asp Gly Thr Leu Asp Gln Val
            260                 265                 270

Trp Asp Tyr Lys Ala Lys Lys Ser Lys Gly Lys Met Thr Ala Ala Glu
        275                 280                 285

Tyr Lys Asp Tyr Tyr Thr Thr Gly
    290                 295

<210> SEQ ID NO 11
<211> LENGTH: 894
<212> TYPE: DNA
<213> ORGANISM: Streptococcus constellatus subsp. constellatus

<400> SEQUENCE: 11
tctaaaaaag taaccattgt taaaggaact ggtaacatgc tacttgtagc aggagctgga       60
catgaccatc accatgagga tgctgacaaa aagcatgagc ataataaaca tagcgaagaa      120
ggacacaacc atgcttttga cccacacgtg tggttgtcac cataccgtag cattacggtc      180
gttgaaaata ttcgcgacag tctttcaaaa gcttacccag aaaaagcaga gaacttcaaa      240
gccaatgccg ctacttatat tgaaaaatta aagagcttg acaaagacta tacggcagca      300 cttttcagatg ctaagcaaaa gagctttgtc actcaacatg ctgcttttgg ctacatggca      360
cttgactatg gcttgaacca aatttctatt aatggtgtca ccagatgc agaaccatca      420 gcaaaacgta ttgctacttt gtcaaaatac gttaaaaaat atggcatcaa atacatttat      480
tttgaggaaa atgcttcaaa taaggtagct aaaacgttag ctaaggaagc aggagttaaa      540
acagctgttc ttagtcctct tgaaggctta acagaaaaag aaatgaaagc aggcgaagat      600
tactttacag tcatgcgcaa aaaccttgaa acattacgct tgacgactga tgttgccggt      660
aaagaaatcc ttccagaaga gataccact aagacagtgt ataatggtta cttcaaagat      720
aaagatgtca aagaccgtaa attatctgac tggtctggta actggcagtc tgtttaccca      780
taccttcaag atggcacttt agaccaagtt tgggattaca aggctaaaaa atctaaaggt      840
aaaatgacag cagctgaata caaagattac tacactactg gttacaaaac tgat             894

<210> SEQ ID NO 12
<211> LENGTH: 298
<212> TYPE: PRT
<213> ORGANISM: Streptococcus constellatus subsp. constellatus

<400> SEQUENCE: 12

Ser Lys Lys Val Thr Ile Val Lys Gly Thr Gly Asn Met Leu Leu Val
1               5                   10                  15

Ala Gly Ala Gly His Asp His His Glu Asp Ala Asp Lys Lys His
            20                  25                  30

Glu His Asn Lys His Ser Glu Glu Gly His Asn His Ala Phe Asp Pro
        35                  40                  45

His Val Trp Leu Ser Pro Tyr Arg Ser Ile Thr Val Val Glu Asn Ile
    50                  55                  60

Arg Asp Ser Leu Ser Lys Ala Tyr Pro Glu Lys Ala Glu Asn Phe Lys
65                  70                  75                  80

Ala Asn Ala Ala Thr Tyr Ile Glu Lys Leu Lys Glu Leu Asp Lys Asp
                85                  90                  95

Tyr Thr Ala Ala Leu Ser Asp Ala Lys Gln Lys Ser Phe Val Thr Gln
```

```
                    100                 105                 110
His Ala Ala Phe Gly Tyr Met Ala Leu Asp Tyr Gly Leu Asn Gln Ile
            115                 120                 125

Ser Ile Asn Gly Val Thr Pro Asp Ala Glu Pro Ser Ala Lys Arg Ile
        130                 135                 140

Ala Thr Leu Ser Lys Tyr Val Lys Lys Tyr Gly Ile Lys Tyr Ile Tyr
145                 150                 155                 160

Phe Glu Glu Asn Ala Ser Asn Lys Val Ala Lys Thr Leu Ala Lys Glu
                165                 170                 175

Ala Gly Val Lys Thr Ala Val Leu Ser Pro Leu Glu Gly Leu Thr Glu
            180                 185                 190

Lys Glu Met Lys Ala Gly Glu Asp Tyr Phe Thr Val Met Arg Lys Asn
        195                 200                 205

Leu Glu Thr Leu Arg Leu Thr Thr Asp Val Ala Gly Lys Glu Ile Leu
210                 215                 220

Pro Glu Glu Asp Thr Thr Lys Thr Val Tyr Asn Gly Tyr Phe Lys Asp
225                 230                 235                 240

Lys Asp Val Lys Asp Arg Lys Leu Ser Asp Trp Ser Gly Asn Trp Gln
                245                 250                 255

Ser Val Tyr Pro Tyr Leu Gln Asp Gly Thr Leu Asp Gln Val Trp Asp
            260                 265                 270

Tyr Lys Ala Lys Lys Ser Lys Gly Lys Met Thr Ala Ala Glu Tyr Lys
        275                 280                 285

Asp Tyr Tyr Thr Thr Gly Tyr Lys Thr Asp
    290                 295

<210> SEQ ID NO 13
<211> LENGTH: 284
<212> TYPE: PRT
<213> ORGANISM: Artificial
<220> FEATURE:
<223> OTHER INFORMATION: consensus
<220> FEATURE:
<221> NAME/KEY: UNSURE
<222> LOCATION: (137)..(137)
<223> OTHER INFORMATION: Xaa=Thr or Ala

<400> SEQUENCE: 13

Ser Lys Lys Val Thr Ile Val Lys Gly Thr Gly Asn Met Leu Leu Val
1               5                   10                  15

Ala Gly Ala Gly His Asp His His Glu Asp Ala Asp Lys Lys His
            20                  25                  30

Glu His Asn Lys His Ser Glu Glu Gly His Asn His Ala Phe Asp Pro
        35                  40                  45

His Val Trp Leu Ser Pro Tyr Arg Ser Ile Thr Val Val Glu Asn Ile
    50                  55                  60

Arg Asp Ser Leu Ser Lys Ala Tyr Pro Glu Lys Ala Glu Asn Phe Lys
65                  70                  75                  80

Ala Asn Ala Ala Thr Tyr Ile Glu Lys Leu Lys Glu Leu Asp Lys Asp
                85                  90                  95

Tyr Thr Ala Ala Leu Ser Asp Ala Lys Gln Lys Ser Phe Val Thr Gln
            100                 105                 110

His Ala Ala Phe Gly Tyr Met Ala Leu Asp Tyr Gly Leu Asn Gln Ile
        115                 120                 125

Ser Ile Asn Gly Val Thr Pro Asp Xaa Glu Pro Ser Ala Lys Arg Ile
    130                 135                 140

Ala Thr Leu Ser Lys Tyr Val Lys Lys Tyr Gly Ile Lys Tyr Ile Tyr
```

```
                145                 150                 155                 160
Phe Glu Glu Asn Ala Ser Asn Lys Val Ala Lys Thr Leu Ala Lys Glu
                165                 170                 175

Ala Gly Val Lys Thr Ala Val Leu Ser Pro Leu Glu Gly Leu Thr Glu
            180                 185                 190

Lys Glu Met Lys Ala Gly Glu Asp Tyr Phe Thr Val Met Arg Lys Asn
        195                 200                 205

Leu Glu Thr Leu Arg Leu Thr Thr Asp Val Ala Gly Lys Glu Ile Leu
    210                 215                 220

Pro Glu Glu Asp Thr Thr Lys Thr Val Tyr Asn Gly Tyr Phe Lys Asp
225                 230                 235                 240

Lys Asp Val Lys Asp Arg Lys Leu Ser Asp Trp Ser Gly Asn Trp Gln
                245                 250                 255

Ser Val Tyr Pro Tyr Leu Gln Asp Gly Thr Leu Asp Gln Val Trp Asp
                260                 265                 270

Tyr Lys Ala Lys Lys Ser Lys Gly Lys Met Thr Ala
            275                 280

<210> SEQ ID NO 14
<211> LENGTH: 25
<212> TYPE: DNA
<213> ORGANISM: Artificial
<220> FEATURE:
<223> OTHER INFORMATION: Primer D1358-F

<400> SEQUENCE: 14
gcaggwacrg arcckcatga ttttg                                              25

<210> SEQ ID NO 15
<211> LENGTH: 16
<212> TYPE: DNA
<213> ORGANISM: Artificial
<220> FEATURE:
<223> OTHER INFORMATION: Primer D1358-F3

<400> SEQUENCE: 15
acgtrtggtt gtcwcc                                                        16

<210> SEQ ID NO 16
<211> LENGTH: 22
<212> TYPE: DNA
<213> ORGANISM: Artificial
<220> FEATURE:
<223> OTHER INFORMATION: Primer D1358-F5

<400> SEQUENCE: 16
gctgtbctta gyccrcttga ag                                                 22

<210> SEQ ID NO 17
<211> LENGTH: 22
<212> TYPE: DNA
<213> ORGANISM: Artificial
<220> FEATURE:
<223> OTHER INFORMATION: Primer D1358-R2

<400> SEQUENCE: 17
cttcaagygg rctaagvaca gc                                                 22

<210> SEQ ID NO 18
<211> LENGTH: 20
<212> TYPE: DNA
<213> ORGANISM: Artificial
<220> FEATURE:
```

```
<223> OTHER INFORMATION: Primer D1358-R3

<400> SEQUENCE: 18
gcdgtcatwt ydyytttaga                                              20

<210> SEQ ID NO 19
<211> LENGTH: 23
<212> TYPE: DNA
<213> ORGANISM: Artificial
<220> FEATURE:
<223> OTHER INFORMATION: Primer D1358-R5

<400> SEQUENCE: 19
gcrtytkbyt cyttagcytc aaa                                          23

<210> SEQ ID NO 20
<211> LENGTH: 23
<212> TYPE: DNA
<213> ORGANISM: Artificial
<220> FEATURE:
<223> OTHER INFORMATION: ATCC12394-1358-F

<400> SEQUENCE: 20
cagatgcgtt cgtttatatg gac                                          23

<210> SEQ ID NO 21
<211> LENGTH: 20
<212> TYPE: DNA
<213> ORGANISM: Artificial
<220> FEATURE:
<223> OTHER INFORMATION: ATCC12394-1358-R

<400> SEQUENCE: 21
cgcacaaatg tcatggtgtt                                              20

<210> SEQ ID NO 22
<211> LENGTH: 515
<212> TYPE: PRT
<213> ORGANISM: Streptococcus pyogenes

<400> SEQUENCE: 22
```

Met Lys Lys Lys Ile Leu Leu Met Met Ser Leu Ile Ser Val Phe Phe
1               5                   10                  15

Ala Trp Gln Leu Thr Gln Ala Lys Gln Val Leu Ala Glu Gly Lys Val
            20                  25                  30

Lys Val Val Thr Thr Phe Tyr Pro Val Tyr Glu Phe Thr Lys Gly Val
        35                  40                  45

Ile Gly Asn Asp Gly Asp Val Phe Met Leu Met Lys Ala Gly Thr Glu
    50                  55                  60

Pro His Asp Phe Glu Pro Ser Thr Lys Asp Ile Lys Lys Ile Gln Asp
65                  70                  75                  80

Ala Asp Ala Phe Val Tyr Met Asp Asp Asn Met Glu Thr Trp Val Ser
                85                  90                  95

Asp Val Lys Lys Ser Leu Thr Ser Lys Lys Val Thr Ile Val Lys Gly
            100                 105                 110

Thr Gly Asn Met Leu Leu Val Ala Gly Ala Gly His Asp His Pro His
        115                 120                 125

Glu Asp Ala Asp Lys Lys His Glu Asn Lys His Ser Glu Glu Gly
    130                 135                 140

His Asn His Ala Phe Asp Pro His Val Trp Leu Ser Pro Tyr Arg Ser
145                 150                 155                 160

```
Ile Thr Val Val Glu Asn Ile Arg Asp Ser Leu Ser Lys Ala Tyr Pro
            165                 170                 175

Glu Lys Ala Glu Asn Phe Lys Ala Asn Ala Ala Thr Tyr Ile Glu Lys
        180                 185                 190

Leu Lys Glu Leu Asp Lys Asp Tyr Thr Ala Ala Leu Ser Asp Ala Lys
    195                 200                 205

Gln Lys Ser Phe Val Thr Gln His Ala Ala Phe Gly Tyr Met Ala Leu
210                 215                 220

Asp Tyr Gly Leu Asn Gln Ile Ser Ile Asn Gly Val Thr Pro Asp Ala
225                 230                 235                 240

Glu Pro Ser Ala Lys Arg Ile Ala Thr Leu Ser Lys Tyr Val Lys Lys
                245                 250                 255

Tyr Gly Ile Lys Tyr Ile Tyr Phe Glu Glu Asn Ala Ser Ser Lys Val
            260                 265                 270

Ala Lys Thr Leu Ala Lys Glu Ala Gly Val Lys Ala Ala Val Leu Ser
        275                 280                 285

Pro Leu Glu Gly Leu Thr Glu Lys Glu Met Lys Ala Gly Gln Asp Tyr
    290                 295                 300

Phe Thr Val Met Arg Lys Asn Leu Glu Thr Leu Arg Leu Thr Thr Asp
305                 310                 315                 320

Val Ala Gly Lys Glu Ile Leu Pro Glu Lys Asp Thr Thr Lys Thr Val
                325                 330                 335

Tyr Asn Gly Tyr Phe Lys Asp Lys Glu Val Lys Asp Arg Gln Leu Ser
            340                 345                 350

Asp Trp Ser Gly Ser Trp Gln Ser Val Tyr Pro Tyr Leu Gln Asp Gly
        355                 360                 365

Thr Leu Asp Gln Val Trp Asp Tyr Lys Ala Lys Ser Lys Gly Lys
    370                 375                 380

Met Thr Ala Ala Glu Tyr Lys Asp Tyr Tyr Thr Gly Tyr Lys Thr
385                 390                 395                 400

Asp Val Glu Gln Ile Lys Ile Asn Gly Lys Lys Lys Thr Met Thr Phe
                405                 410                 415

Val Arg Asn Gly Glu Lys Lys Thr Phe Thr Tyr Thr Tyr Ala Gly Lys
            420                 425                 430

Glu Ile Leu Thr Tyr Pro Lys Gly Asn Arg Gly Val Arg Phe Met Phe
        435                 440                 445

Glu Ala Lys Glu Ala Asp Ala Gly Glu Phe Lys Tyr Val Gln Phe Ser
    450                 455                 460

Asp His Ala Ile Ala Pro Glu Lys Ala Lys His Phe His Leu Tyr Trp
465                 470                 475                 480

Gly Gly Asp Ser Gln Glu Lys Leu His Lys Glu Leu Glu His Trp Pro
                485                 490                 495

Thr Tyr Tyr Gly Ser Asp Leu Ser Gly Arg Glu Ile Ala Gln Glu Ile
            500                 505                 510

Asn Ala His
        515

<210> SEQ ID NO 23
<211> LENGTH: 506
<212> TYPE: PRT
<213> ORGANISM: Streptococcus agalactiae

<400> SEQUENCE: 23

Met Arg Lys Lys Phe Leu Leu Leu Met Ser Phe Val Ala Met Phe Ala
1               5                   10                  15
```

```
Ala Trp Gln Leu Val Gln Val Lys Gln Val Trp Ala Asp Ser Lys Leu
             20                  25                  30

Lys Val Val Thr Thr Phe Tyr Pro Val Tyr Glu Phe Thr Lys Asn Val
         35                  40                  45

Val Gly Asp Lys Ala Asp Val Ser Met Leu Ile Lys Ala Gly Thr Glu
 50                  55                  60

Pro His Asp Phe Glu Pro Ser Thr Lys Asn Ile Ala Ala Ile Gln Asp
 65                  70                  75                  80

Ser Asn Ala Phe Val Tyr Met Asp Asp Asn Met Glu Thr Trp Ala Pro
             85                  90                  95

Lys Val Ala Lys Ser Val Lys Ser Lys Lys Val Thr Thr Ile Lys Gly
            100                 105                 110

Thr Gly Asp Met Leu Leu Thr Lys Gly Val Glu Glu Glu Gly Glu Glu
            115                 120                 125

His Glu Gly His Gly His Glu Gly His His His Glu Leu Asp Pro His
        130                 135                 140

Val Trp Leu Ser Pro Glu Arg Ala Ile Ser Val Val Glu Asn Ile Arg
145                 150                 155                 160

Asn Lys Phe Val Lys Ala Tyr Pro Lys Asp Ala Ala Ser Phe Asn Lys
                165                 170                 175

Asn Ala Asp Ala Tyr Ile Ala Lys Leu Lys Glu Leu Asp Lys Glu Tyr
            180                 185                 190

Lys Asn Gly Leu Ser Asn Ala Lys Gln Lys Ser Phe Val Thr Gln His
        195                 200                 205

Ala Ala Phe Gly Tyr Met Ala Leu Asp Tyr Gly Leu Asn Gln Val Pro
210                 215                 220

Ile Ala Gly Leu Thr Pro Asp Ala Glu Pro Ser Ser Lys Arg Leu Gly
225                 230                 235                 240

Glu Leu Ala Lys Tyr Ile Lys Lys Tyr Asn Ile Asn Tyr Ile Tyr Phe
                245                 250                 255

Glu Glu Asn Ala Ser Asn Lys Val Ala Lys Thr Leu Ala Asp Glu Val
            260                 265                 270

Gly Val Lys Thr Ala Val Leu Ser Pro Leu Gly Leu Ser Lys Lys
        275                 280                 285

Glu Met Ala Ala Gly Glu Asp Tyr Phe Ser Val Met Arg Arg Asn Leu
290                 295                 300

Lys Val Leu Lys Lys Thr Thr Asp Val Ala Gly Lys Glu Val Ala Pro
305                 310                 315                 320

Glu Glu Asp Lys Thr Lys Thr Val Glu Thr Gly Tyr Phe Lys Thr Lys
                325                 330                 335

Asp Val Lys Asp Arg Lys Leu Thr Asp Tyr Ser Gly Asn Trp Gln Ser
            340                 345                 350

Val Tyr Pro Leu Leu Gln Asp Gly Thr Leu Asp Pro Val Trp Asp Tyr
        355                 360                 365

Lys Ala Lys Ser Lys Lys Asp Met Thr Ala Ala Glu Tyr Lys Lys Tyr
370                 375                 380

Tyr Thr Ala Gly Tyr Lys Thr Asp Val Glu Ser Ile Lys Ile Asp Gly
385                 390                 395                 400

Lys Lys His Gln Met Thr Phe Val Arg Asn Gly Lys Ser Gln Thr Phe
                405                 410                 415

Thr Tyr Lys Tyr Ala Gly Tyr Lys Ile Leu Thr Tyr Lys Lys Gly Asn
            420                 425                 430

Arg Gly Val Arg Tyr Leu Phe Glu Ala Lys Glu Lys Asp Ala Gly Gln
        435                 440                 445
```

```
Phe Lys Tyr Ile Gln Phe Ser Asp His Gly Ile Lys Pro Asn Lys Ala
    450                 455                 460
Glu His Phe His Ile Phe Trp Gly Ser Glu Ser Gln Glu Lys Leu Phe
465                 470                 475                 480
Glu Glu Met Glu Asn Trp Pro Thr Tyr Phe Pro Ala Lys Met Ser Gly
                485                 490                 495
Arg Glu Val Ala Gln Asp Leu Met Ser His
            500                 505

<210> SEQ ID NO 24
<211> LENGTH: 506
<212> TYPE: PRT
<213> ORGANISM: Streptococcus agalactiae

<400> SEQUENCE: 24

Met Arg Lys Lys Phe Leu Leu Met Ser Phe Val Ala Met Phe Ala
1               5                   10                  15
Ala Trp Gln Leu Val Gln Val Lys Gln Val Trp Ala Asp Ser Lys Leu
        20                  25                  30
Lys Val Val Thr Thr Phe Tyr Pro Val Tyr Glu Phe Thr Lys Asn Val
            35                  40                  45
Val Gly Asp Lys Ala Asp Val Ser Met Leu Ile Lys Ala Gly Thr Glu
50                  55                  60
Pro His Asp Phe Glu Pro Ser Thr Lys Asn Ile Ala Ala Ile Gln Asp
65                  70                  75                  80
Ser Asn Ala Phe Val Tyr Met Asp Asp Asn Met Glu Thr Trp Ala Pro
                85                  90                  95
Lys Val Ala Lys Ser Val Lys Ser Lys Lys Val Thr Thr Ile Lys Gly
            100                 105                 110
Thr Gly Asp Met Leu Leu Thr Lys Gly Val Glu Glu Glu Gly Glu Glu
        115                 120                 125
His Glu Gly His Gly His Glu Gly His His Glu Leu Asp Pro His
    130                 135                 140
Val Trp Leu Ser Pro Glu Arg Ala Ile Ser Val Val Glu Asn Ile Arg
145                 150                 155                 160
Asn Lys Phe Val Lys Ala Tyr Pro Lys Asp Ala Ala Ser Phe Asn Lys
                165                 170                 175
Asn Ala Asp Ala Tyr Ile Ala Lys Leu Lys Glu Leu Asp Lys Glu Tyr
            180                 185                 190
Lys Asn Gly Leu Ser Asn Ala Lys Gln Lys Ser Phe Val Thr Gln His
        195                 200                 205
Ala Ala Phe Gly Tyr Met Ala Leu Asp Tyr Gly Leu Asn Gln Val Pro
    210                 215                 220
Ile Ala Gly Leu Thr Pro Asp Ala Glu Pro Ser Ser Lys Arg Leu Gly
225                 230                 235                 240
Glu Leu Ala Lys Tyr Ile Lys Lys Tyr Asn Ile Asn Tyr Ile Tyr Phe
                245                 250                 255
Glu Glu Asn Ala Ser Asn Lys Val Ala Lys Thr Leu Ala Asp Glu Val
            260                 265                 270
Gly Val Lys Thr Ala Val Leu Ser Pro Leu Glu Gly Leu Ser Lys Lys
        275                 280                 285
Glu Met Ala Ala Gly Glu Asp Tyr Phe Ser Val Met Arg Arg Asn Leu
    290                 295                 300
Lys Val Leu Lys Lys Thr Thr Asp Val Ala Gly Lys Glu Val Ala Pro
305                 310                 315                 320
```

```
Glu Glu Asp Lys Thr Lys Thr Val Glu Thr Gly Tyr Phe Lys Thr Lys
                325                 330                 335
Asp Val Lys Asp Arg Lys Leu Thr Asp Tyr Ser Gly Asn Trp Gln Ser
            340                 345                 350
Val Tyr Pro Leu Leu Gln Asp Gly Thr Leu Asp Pro Val Trp Asp Tyr
        355                 360                 365
Lys Ala Lys Ser Lys Lys Asp Met Thr Ala Ala Glu Tyr Lys Lys Tyr
    370                 375                 380
Tyr Thr Ala Gly Tyr Lys Thr Asp Val Glu Ser Ile Lys Ile Asp Gly
385                 390                 395                 400
Lys Lys His Gln Met Thr Phe Val Arg Asn Gly Lys Ser Gln Thr Phe
                405                 410                 415
Thr Tyr Lys Tyr Ala Gly Tyr Lys Ile Leu Thr Tyr Lys Lys Gly Asn
            420                 425                 430
Arg Gly Val Arg Tyr Leu Phe Glu Ala Lys Glu Lys Asp Ala Gly Gln
        435                 440                 445
Phe Lys Tyr Ile Gln Phe Ser Asp His Gly Ile Lys Pro Asn Lys Ala
    450                 455                 460
Glu His Phe His Ile Phe Trp Gly Ser Glu Ser Gln Glu Lys Leu Phe
465                 470                 475                 480
Glu Glu Met Glu Asn Trp Pro Thr Tyr Phe Pro Ala Lys Met Ser Gly
                485                 490                 495
Arg Glu Val Ala Gln Asp Leu Met Ser His
            500                 505

<210> SEQ ID NO 25
<211> LENGTH: 1548
<212> TYPE: DNA
<213> ORGANISM: Streptococcus equisimilis

<400> SEQUENCE: 25
atgaagaaga aaattctttt aatgattagt ttaatcggtg tgttttttgc ttggcaactt      60
agccaagcaa acaagtgttt agcagagggt aaagttaagg ttgtcacaac tttctaccct     120
gtctacgaat ttacaaaagg tgttattggt aatgatggcg atgtctcact attgatgaag     180
gcaggaacag agcctcatga tttttgaaccg tcaaccaaag acattaaaaa aattcaagat     240
gcagatgcgt tcgtttatat ggacgacaac atggaaacat ggatttctga tgttaaaaaa     300
tcattgaaat ctaaaaaagt aaccattgtt aaaggaactg gtaacatgct acttgtagca     360
ggagctggac atgaccatca ccatgaggat gctgacaaaa agcatgagca taataaacat     420
agcgaagaag acacaaccca tgcttttgac ccacacgtgt ggttgtcacc ataccgtagc     480
attacggtcg ttgaaaatat tcgcgacagt ctttcaaaag cttacccaga aaaagcagag     540
aacttcaaag ccaatgccgc tacttatatt gaaaaattaa aagagcttga caaagactat     600
acggcagcac tttcagatgc taagcaaaag agctttgtca ctcaacatgc tgcttttggc     660
tacatggcac ttgactatgg cttgaaccaa atttctatta atggtgtcac accagatgca     720
gaaccatcag caaaacgtat tgctactttg tcaaaatacg ttaaaaaata tggcatcaaa     780
tacatttatt ttgaggaaaa tgcttcaaat aaggtagcta aacgttagc taaggaagca     840
ggagttaaaa cagctgttct tagtcctctt gaaggcttaa cagaaaaaga atgaaagca      900
ggcgaagatt actttacagt catgcgcaaa accttgaaa cattacgctt gacgactgat     960
gttgccggta agaaatcct tccagaagaa gataccacta gacagtgta atggttac      1020
ttcaaagata aagatgtcaa agaccgtaaa ttatctgact ggtctggtaa ctggcagtct     1080
```

```
gtttacccat accttcaaga tggcacttta gaccaagttt gggattacaa ggctaaaaaa      1140
tctaaaggta aaatgacagc agctgaatac aaagattact acactactgg ttacaaaact      1200
gatgtggagc aaatcaacat taatggtaag aaaaacacca tgacatttgt gcgaaatggt      1260
gaaaagaaaa cctttactta caaatatgct ggtaaagaaa tattgactta ccaaaagga      1320 aatcgtgggg ttcgtttcat gtttgaagct aagaagcag atgctggcga attcaaatac        1380
gttcaattca gtgaccatgc cattgctccg gaaaaagcag agcatttcca cttgtattgg      1440
ggtggtgata gccaagaaaa attacataaa gagttagaac attggccaac ttactacggt      1500
tcagacttat ctggtcgtga aattgcccaa gaaattaacg ctcattaa                    1548
```

<210> SEQ ID NO 26
<211> LENGTH: 515
<212> TYPE: PRT
<213> ORGANISM: Streptococcus equisimilis

<400> SEQUENCE: 26

```
Met Lys Lys Lys Ile Leu Leu Met Ile Ser Leu Ile Gly Val Phe Phe
1               5                   10                  15

Ala Trp Gln Leu Ser Gln Ala Lys Gln Val Leu Ala Glu Gly Lys Val
            20                  25                  30

Lys Val Val Thr Thr Phe Tyr Pro Val Tyr Glu Phe Thr Lys Gly Val
        35                  40                  45

Ile Gly Asn Asp Gly Asp Val Ser Leu Leu Met Lys Ala Gly Thr Glu
    50                  55                  60

Pro His Asp Phe Glu Pro Ser Thr Lys Asp Ile Lys Lys Ile Gln Asp
65                  70                  75                  80

Ala Asp Ala Phe Val Tyr Met Asp Asp Asn Met Glu Thr Trp Ile Ser
                85                  90                  95

Asp Val Lys Lys Ser Leu Lys Ser Lys Lys Val Thr Ile Val Lys Gly
            100                 105                 110

Thr Gly Asn Met Leu Leu Val Ala Gly Ala Gly His Asp His His His
        115                 120                 125

Glu Asp Ala Asp Lys Lys His Glu His Asn Lys His Ser Glu Glu Gly
    130                 135                 140

His Asn His Ala Phe Asp Pro His Val Trp Leu Ser Pro Tyr Arg Ser
145                 150                 155                 160

Ile Thr Val Val Glu Asn Ile Arg Asp Ser Leu Ser Lys Ala Tyr Pro
                165                 170                 175

Glu Lys Ala Glu Asn Phe Lys Ala Asn Ala Ala Thr Tyr Ile Glu Lys
            180                 185                 190

Leu Lys Glu Leu Asp Lys Asp Tyr Thr Ala Ala Leu Ser Asp Ala Lys
        195                 200                 205

Gln Lys Ser Phe Val Thr Gln His Ala Ala Phe Gly Tyr Met Ala Leu
    210                 215                 220

Asp Tyr Gly Leu Asn Gln Ile Ser Ile Asn Gly Val Thr Pro Asp Ala
225                 230                 235                 240

Glu Pro Ser Ala Lys Arg Ile Ala Thr Leu Ser Lys Tyr Val Lys Lys
                245                 250                 255

Tyr Gly Ile Lys Tyr Ile Tyr Phe Glu Glu Asn Ala Ser Asn Lys Val
            260                 265                 270

Ala Lys Thr Leu Ala Lys Glu Ala Gly Val Lys Thr Ala Val Leu Ser
        275                 280                 285

Pro Leu Glu Gly Leu Thr Glu Lys Glu Met Lys Ala Gly Glu Asp Tyr
```

```
                  290                 295                 300
Phe Thr Val Met Arg Lys Asn Leu Glu Thr Leu Arg Leu Thr Thr Asp
305                 310                 315                 320

Val Ala Gly Lys Glu Ile Leu Pro Glu Glu Asp Thr Thr Lys Thr Val
                325                 330                 335

Tyr Asn Gly Tyr Phe Lys Asp Lys Asp Val Lys Asp Arg Lys Leu Ser
                340                 345                 350

Asp Trp Ser Gly Asn Trp Gln Ser Val Tyr Pro Tyr Leu Gln Asp Gly
            355                 360                 365

Thr Leu Asp Gln Val Trp Asp Tyr Lys Ala Lys Ser Lys Gly Lys
    370                 375                 380

Met Thr Ala Ala Glu Tyr Lys Asp Tyr Tyr Thr Gly Tyr Lys Thr
385                 390                 395                 400

Asp Val Glu Gln Ile Asn Ile Asn Gly Lys Lys Asn Thr Met Thr Phe
                405                 410                 415

Val Arg Asn Gly Glu Lys Lys Thr Phe Thr Tyr Lys Tyr Ala Gly Lys
                420                 425                 430

Glu Ile Leu Thr Tyr Pro Lys Gly Asn Arg Gly Val Arg Phe Met Phe
            435                 440                 445

Glu Ala Lys Glu Ala Asp Ala Gly Glu Phe Lys Tyr Val Gln Phe Ser
450                 455                 460

Asp His Ala Ile Ala Pro Glu Lys Ala Glu His Phe His Leu Tyr Trp
465                 470                 475                 480

Gly Gly Asp Ser Gln Glu Lys Leu His Lys Glu Leu Glu His Trp Pro
            485                 490                 495

Thr Tyr Tyr Gly Ser Asp Leu Ser Gly Arg Glu Ile Ala Gln Glu Ile
            500                 505                 510

Asn Ala His
        515

<210> SEQ ID NO 27
<211> LENGTH: 1548
<212> TYPE: DNA
<213> ORGANISM: Streptococcus equisimilis

<400> SEQUENCE: 27
atgaagaaga aaattctttt aatgattagt ttaatcggtg tgttttttgc ttggcaactt      60
agccaagcaa acaagtgtt agcagagggt aaagttaagg ttgtcacaac tttctaccct     120
gtctacgaat ttacaaaagg tgttattggt aatgatggcg atgtttccat gcttatgaaa     180
gcaggaacag agcctcatga ttttgaaccg tcaaccaaag acattaaaaa aattcaagat     240
gcagatgcgt tcgtttatat ggacgacaac atggaaacat ggatttctga tgttaaaaaa     300
tcattgacat ctaaaaaagt aaccattgtt aaaggaactg gtaacatgct acttgtagca     360
ggagctggac atgaccatca ccatgaggat gctgacaaaa agcatgagca ataaaaacat     420
agcgaagaag gacacaacca tgcttttgac ccacacgtgt ggttgtcacc ataccgtagc     480
attacggtcg ttgaaaatat tcgcgacagt ctttcaaaag cttacccaga aaagcagaa      540 aacttcaaag ccaatgccgc tactatatt gaaaaattaa agagcttga caaagactat      600 acggcagcac tttcagatgc taagcaaaag agctttgtca ctcaacatgc tgcttttggc     660
tacatggcac ttgactatgg cttgaaccaa atttctatta tggtgtcac accagataca      720 gaaccatcag caaacgtat tgctactttg tcaaatacg ttaaaaaata tggcatcaaa      780
tacatttatt ttgaggaaaa tgcttcaat aaggtagcta aacgttagc taaggaagca      840
```

| | | |
|---|---|---|
| ggagttaaaa cagctgttct tagtcctctt gaaggcttaa cagaaaaaga aatgaaagca | 900 |
| ggcgaagatt actttacagt catgcgcaaa aaccttgaaa cattacgctt gacgactgat | 960 |
| gttgccggta agaaatcct tccagaagaa gataccacta agacagtgta taatggttac | 1020 |
| ttcaaagata aagatgtcaa agaccgtaaa ttatctgact ggtctggtaa ctggcagtct | 1080 |
| gtttacccat accttcaaga tggcacttta gaccaagttt gggattacaa ggctaaaaaa | 1140 |
| tctaaaggta aaatgacagc agctgaatac aaagattact acactactgg ttacaaaact | 1200 |
| gatgtggagc aaatcaacat taatggtaag aaaaacacca tgacatttgt gcgaaatggt | 1260 |
| gaaaagaaaa cctttactta caaatatgct ggtaaagaaa tattgactta tccaaaagga | 1320 |
| aatcgtgggg ttcgtttcat gtttgaagct aaagaagcag atgctggcga attcaaatac | 1380 |
| gttcaattca gtgaccatgc cattgctccg gaaaaagcag agcatttcca cttgtattgg | 1440 |
| ggtggtgata gccaagaaaa attacataaa gagttagaac attggccaac ttactacggt | 1500 |
| tcagacttat ctggtcgtga aattgcccag gaaattaacg ctcattaa | 1548 |

<210> SEQ ID NO 28
<211> LENGTH: 515
<212> TYPE: PRT
<213> ORGANISM: Streptococcus equisimilis

<400> SEQUENCE: 28

```
Met Lys Lys Lys Ile Leu Leu Met Ile Ser Leu Ile Gly Val Phe Phe
1               5                   10                  15

Ala Trp Gln Leu Ser Gln Ala Lys Gln Val Leu Ala Glu Gly Lys Val
            20                  25                  30

Lys Val Val Thr Thr Phe Tyr Pro Val Tyr Glu Phe Thr Lys Gly Val
        35                  40                  45

Ile Gly Asn Asp Gly Asp Val Ser Met Leu Met Lys Ala Gly Thr Glu
    50                  55                  60

Pro His Asp Phe Glu Pro Ser Thr Lys Asp Ile Lys Lys Ile Gln Asp
65                  70                  75                  80

Ala Asp Ala Phe Val Tyr Met Asp Asp Asn Met Glu Thr Trp Ile Ser
                85                  90                  95

Asp Val Lys Lys Ser Leu Thr Ser Lys Lys Val Thr Ile Val Lys Gly
            100                 105                 110

Thr Gly Asn Met Leu Leu Val Ala Gly Ala Gly His Asp His His His
        115                 120                 125

Glu Asp Ala Asp Lys Lys His Glu His Asn Lys His Ser Glu Glu Gly
    130                 135                 140

His Asn His Ala Phe Asp Pro His Val Trp Leu Ser Pro Tyr Arg Ser
145                 150                 155                 160

Ile Thr Val Val Glu Asn Ile Arg Asp Ser Leu Ser Lys Ala Tyr Pro
                165                 170                 175

Glu Lys Ala Glu Asn Phe Lys Ala Asn Ala Ala Thr Tyr Ile Glu Lys
            180                 185                 190

Leu Lys Glu Leu Asp Lys Asp Tyr Thr Ala Ala Leu Ser Asp Ala Lys
        195                 200                 205

Gln Lys Ser Phe Val Thr Gln His Ala Ala Phe Gly Tyr Met Ala Leu
    210                 215                 220

Asp Tyr Gly Leu Asn Gln Ile Ser Ile Asn Gly Val Thr Pro Asp Thr
225                 230                 235                 240

Glu Pro Ser Ala Lys Arg Ile Ala Thr Leu Ser Lys Tyr Val Lys Lys
                245                 250                 255
```

```
Tyr Gly Ile Lys Tyr Ile Tyr Phe Glu Glu Asn Ala Ser Asn Lys Val
            260                 265                 270
Ala Lys Thr Leu Ala Lys Glu Ala Gly Val Lys Thr Ala Val Leu Ser
        275                 280                 285
Pro Leu Glu Gly Leu Thr Glu Lys Glu Met Lys Ala Gly Glu Asp Tyr
    290                 295                 300
Phe Thr Val Met Arg Lys Asn Leu Glu Thr Leu Arg Leu Thr Thr Asp
305                 310                 315                 320
Val Ala Gly Lys Glu Ile Leu Pro Glu Glu Asp Thr Thr Lys Thr Val
                325                 330                 335
Tyr Asn Gly Tyr Phe Lys Asp Lys Asp Val Lys Asp Arg Lys Leu Ser
            340                 345                 350
Asp Trp Ser Gly Asn Trp Gln Ser Val Tyr Pro Tyr Leu Gln Asp Gly
        355                 360                 365
Thr Leu Asp Gln Val Trp Asp Tyr Lys Ala Lys Ser Lys Gly Lys
    370                 375                 380
Met Thr Ala Ala Glu Tyr Lys Asp Tyr Tyr Thr Gly Tyr Lys Thr
385                 390                 395                 400
Asp Val Glu Gln Ile Asn Ile Asn Gly Lys Lys Asn Thr Met Thr Phe
                405                 410                 415
Val Arg Asn Gly Glu Lys Lys Thr Phe Thr Tyr Lys Tyr Ala Gly Lys
            420                 425                 430
Glu Ile Leu Thr Tyr Pro Lys Gly Asn Arg Gly Val Arg Phe Met Phe
        435                 440                 445
Glu Ala Lys Glu Ala Asp Ala Gly Glu Phe Lys Tyr Val Gln Phe Ser
    450                 455                 460
Asp His Ala Ile Ala Pro Glu Lys Ala Glu His Phe His Leu Tyr Trp
465                 470                 475                 480
Gly Gly Asp Ser Gln Glu Lys Leu His Lys Glu Leu Glu His Trp Pro
                485                 490                 495
Thr Tyr Tyr Gly Ser Asp Leu Ser Gly Arg Glu Ile Ala Gln Glu Ile
            500                 505                 510
Asn Ala His
        515

<210> SEQ ID NO 29
<211> LENGTH: 1499
<212> TYPE: DNA
<213> ORGANISM: Streptococcus anginosus

<400> SEQUENCE: 29
tgaagaaaat tggtctatta gtagcaagtt tactgagtat cttttagtg gcttgttcca       60 atcaaaaaag tgcaaatggg aaattaaatg ttgtcacaac attttaccca gtttatgaat      120
ttaccaagca agtagcaggc gatactgcca atgtcaaact cttgattggt gcaggaacag      180
aaccgcacga atacgagcct tctgccaagg cagttgcaac gattcaagat gcagatgctt      240 tgtatatga aatgaaaat atggaaactt gggtaccaaa attgctcaaa actttgaaaa        300
aagacaaagt aaatgtggtg aaagcaagtg gaaaaatgtt gcttcttcct ggtacagaag      360
aggaagaaga ccatgatcat gggagcgaag acaccatca tgaatacgat ccccatgtgt      420
ggttgtcacc aaaacgtgcc attaaaatgg tggagaatat tcgtgacagc ttaagtaaac      480
gctatcccga taagaaagcg actttccaaa agaacgcagc agcttacatt aagaaattag      540
aaactctgga taagaatat gcaactggtt tagcaaatgc aaaacaaaaa agttttgtga       600
cgcaacatgc tgcttttcga tatcttgcat tggattatgg tttgaaacaa gttcctattt      660
```

```
caggactttc accagatagt gagccttcag cagcgcgttt ggctgaattg acaaaatata    720
ttaagaaaaa caatatcaag tacatttact ttgaagaaaa tgcttctcaa gctttggcat    780
ctactttggc aaaagaaaca ggtgtgaagt tggatgtgct caatccactt gaaagtctaa    840
cagaaaaaca aaccaaagac ggggcagatt acatttcaat catgaagtcc aacttgaaag    900
ccttgaaaaa gacaaccgat caagcaggcg ctgagatttc tgctgaaaaa gaggaaaata    960
cgaagactgt acaaaatggt tactttgaag atagtgctgt taaagaccgt actttgtctg   1020
actatgcagg tcaatggcaa tcagtttatc catacttaca agatgggact ttagaccaag   1080
tctttgatta caaggcaaaa ttaactggta agatgacagc agctgagtac aaagcctatt   1140
atgaaaaggg ctacaagaca gatgtgtctc atatcaatat cacagataag accatggaat   1200 tgtagtaaa cgggcaaaag aagaaatata cttataaata tgttggtaag catacattga   1260
cgtactctaa agggaaccga ggcgtgcgtt tcatgtttga agcgacagac ccagatgcag   1320
gtaagtataa atatgttcaa tttagcgacc ataaatatcgc cccaacgaaa gcagcgcatt   1380
tccatatctt ctacggcggt gaaagccaag aagccctctt taacgaatta gaaaattggc   1440
caacttacta cccaactaaa ttaagcggac aagaaattgc tcaagaaatg cttgcgcat    1499
```

<210> SEQ ID NO 30
<211> LENGTH: 500
<212> TYPE: PRT
<213> ORGANISM: Streptococcus anginosus

<400> SEQUENCE: 30

```
Met Lys Lys Ile Gly Leu Leu Val Ala Ser Leu Leu Ser Ile Phe Leu
1               5                   10                  15

Val Ala Cys Ser Asn Gln Lys Ser Ala Asn Gly Lys Leu Asn Val Val
            20                  25                  30

Thr Thr Phe Tyr Pro Val Tyr Glu Phe Thr Lys Gln Val Ala Gly Asp
        35                  40                  45

Thr Ala Asn Val Lys Leu Leu Ile Gly Ala Gly Thr Glu Pro His Glu
    50                  55                  60

Tyr Glu Pro Ser Ala Lys Ala Val Ala Thr Ile Gln Asp Ala Asp Ala
65                  70                  75                  80

Phe Val Tyr Glu Asn Glu Asn Met Glu Thr Trp Val Pro Lys Leu Leu
                85                  90                  95

Lys Thr Leu Lys Lys Asp Lys Val Asn Val Val Lys Ala Ser Gly Lys
            100                 105                 110

Met Leu Leu Leu Pro Gly Thr Glu Glu Glu Asp His Asp His Gly
        115                 120                 125

Ser Glu Gly His His His Glu Tyr Asp Pro His Val Trp Leu Ser Pro
    130                 135                 140

Lys Arg Ala Ile Lys Met Val Glu Asn Ile Arg Asp Ser Leu Ser Lys
145                 150                 155                 160

Arg Tyr Pro Asp Lys Lys Ala Thr Phe Gln Lys Asn Ala Ala Ala Tyr
                165                 170                 175

Ile Lys Lys Leu Glu Thr Leu Asp Lys Glu Tyr Ala Thr Gly Leu Ala
            180                 185                 190

Asn Ala Lys Gln Lys Ser Phe Val Thr Gln His Ala Ala Phe Arg Tyr
        195                 200                 205

Leu Ala Leu Asp Tyr Gly Leu Lys Gln Val Pro Ile Ser Gly Leu Ser
    210                 215                 220

Pro Asp Ser Glu Pro Ser Ala Ala Arg Leu Ala Glu Leu Thr Lys Tyr
```

225                 230                 235                 240
        Ile Lys Lys Asn Asn Ile Lys Tyr Ile Tyr Phe Glu Glu Asn Ala Ser
                        245                 250                 255
        Gln Ala Leu Ala Ser Thr Leu Ala Lys Glu Thr Gly Val Lys Leu Asp
                    260                 265                 270
        Val Leu Asn Pro Leu Glu Ser Leu Thr Glu Lys Gln Thr Lys Asp Gly
                275                 280                 285
        Ala Asp Tyr Ile Ser Ile Met Lys Ser Asn Leu Lys Ala Leu Lys Lys
            290                 295                 300
        Thr Thr Asp Gln Ala Gly Ala Glu Ile Ser Ala Glu Lys Glu Asn
        305                 310                 315                 320
        Thr Lys Thr Val Gln Asn Gly Tyr Phe Glu Asp Ser Ala Val Lys Asp
                        325                 330                 335
        Arg Thr Leu Ser Asp Tyr Ala Gly Gln Trp Gln Ser Val Tyr Pro Tyr
                    340                 345                 350
        Leu Gln Asp Gly Thr Leu Asp Gln Val Phe Asp Tyr Lys Ala Lys Leu
                355                 360                 365
        Thr Gly Lys Met Thr Ala Ala Glu Tyr Lys Ala Tyr Glu Lys Gly
            370                 375                 380
        Tyr Lys Thr Asp Val Ser His Ile Asn Ile Thr Asp Lys Thr Met Glu
        385                 390                 395                 400
        Phe Val Val Asn Gly Gln Lys Lys Tyr Thr Tyr Lys Tyr Val Gly
                        405                 410                 415
        Lys His Thr Leu Thr Tyr Ser Lys Gly Asn Arg Gly Val Arg Phe Met
                    420                 425                 430
        Phe Glu Ala Thr Asp Pro Asp Ala Gly Lys Tyr Lys Tyr Val Gln Phe
                435                 440                 445
        Ser Asp His Asn Ile Ala Pro Thr Lys Ala Ala His Phe His Ile Phe
            450                 455                 460
        Tyr Gly Gly Glu Ser Gln Glu Ala Leu Phe Asn Glu Leu Glu Asn Trp
        465                 470                 475                 480
        Pro Thr Tyr Tyr Pro Thr Lys Leu Ser Gly Gln Glu Ile Ala Gln Glu
                        485                 490                 495
        Met Leu Ala His
                500

<210> SEQ ID NO 31
<211> LENGTH: 1500
<212> TYPE: DNA
<213> ORGANISM: Streptococcus constellatus subsp. constellatus

<400> SEQUENCE: 31
atgaagaaaa ttggtctatt agtagcaagc ttactaagtc tcttttagt agcttgttcc      60 aatcaaaaaa gcgcaaatgg gaagctaaat attgtgacaa cattttatcc agtttatgag     120
tttactaagc aagtgacagg tgatactgct aatgttaaat tgctaatcgg tgcagggaca     180
gaaccacatg aatatgaacc ttctgctaag gcggttgcaa cgattcaaga tgcagatact     240
ttcgtttatg aaaatgaaaa catggaaact tgggtgccaa aattgcttaa aaccttgaaa     300
aaaggtaaag tgaatgtggt gaaggcgact gggaagatgt tgctactgcc tggtacagaa     360
gaggaaggag atcatgatca tggtaaagaa ggacatcatc atgaatacga tcctcatgta     420
tggttatcac caaacgtgc tattaaaatg gtggaaaata ttcgtgacag cttaagtaaa     480
cgctatccag ataagaaagc aactttccaa agaacgcag caacttacat taagaaatta     540
gaaactctgg ataagaata tgcaactggt ttagcaaatg caaaacaaaa aagttttgtg     600

```
acgcaacatg ctgcttttcg atatcttgca ttggattatg gtttgaaaca agttcctatt      660
tcagggcttt caccagatag tgagccttca gcagcgcgtt tggctgaatt gacaaaatat      720
attaagaaaa acaatattaa gtatatctat tttgaagaaa atgcttctca agcattggct      780
tctacattgg caaaagaaac aggtgtgaag ttagatgtcc ttaatccgct tgaaagtttg      840
actgaaaagc aaacaaaaga tggggcagac tacatttcaa tcatgaagtc aacttgaaa       900
gccttgaaga agacaactga ccaagcaggc gctgaaattt ctgctgaaaa agaaaaaaat      960
acaaagactg tacaaaatgg ctactttgaa gatagtgctg ttaaagaccg tacgttgtct     1020
gactatgcag gtcaatggca atccgtttat ccatatttgc aagatggaac tttagaccaa     1080
gtctttgatt acaaagcaaa attaagcggt aagatgacag ctgctgagta caaagcgtat     1140
tatgaaaaag gctataagac agatgtgtct catatcaata tcacagataa gactatggaa     1200
tttgtagtca acggacaaaa gaaaaaattt acttacaaat acgttggtaa gcatacattg     1260
acttattcta aaggcaatcg tggtgtgcgt ttcatgtttg aaacaacgga taagatgct       1320
ggaaaatata aatatgtgca attcagcgac cataatattg caccaacgaa agcagcacac     1380
ttccatatct tctatggtgg tgaaaaccaa gaagcacttt tcaacgaatt agaaaattgg     1440
ccaacttact acccaactaa gctgagtgga caagaaatcg cccaagaaat gctcgcacat     1500

<210> SEQ ID NO 32
<211> LENGTH: 500
<212> TYPE: PRT
<213> ORGANISM: Streptococcus constellatus subsp. constellatus

<400> SEQUENCE: 32

Met Lys Lys Ile Gly Leu Leu Val Ala Ser Leu Leu Ser Leu Phe Leu
1               5                   10                  15

Val Ala Cys Ser Asn Gln Lys Ser Ala Asn Gly Lys Leu Asn Ile Val
            20                  25                  30

Thr Thr Phe Tyr Pro Val Tyr Glu Phe Thr Lys Gln Val Thr Gly Asp
        35                  40                  45

Thr Ala Asn Val Lys Leu Leu Ile Gly Ala Gly Thr Glu Pro His Glu
    50                  55                  60

Tyr Glu Pro Ser Ala Lys Ala Val Ala Thr Ile Gln Asp Ala Asp Thr
65                  70                  75                  80

Phe Val Tyr Glu Asn Glu Asn Met Glu Thr Trp Val Pro Lys Leu Leu
                85                  90                  95

Lys Thr Leu Lys Lys Gly Lys Val Asn Val Lys Ala Thr Gly Lys
            100                 105                 110

Met Leu Leu Leu Pro Gly Thr Glu Glu Glu Gly Asp His Asp His Gly
        115                 120                 125

Lys Glu Gly His His His Glu Tyr Asp Pro His Val Trp Leu Ser Pro
    130                 135                 140

Lys Arg Ala Ile Lys Met Val Glu Asn Ile Arg Asp Ser Leu Ser Lys
145                 150                 155                 160

Arg Tyr Pro Asp Lys Lys Ala Thr Phe Gln Lys Asn Ala Ala Thr Tyr
                165                 170                 175

Ile Lys Lys Leu Glu Thr Leu Asp Lys Glu Tyr Ala Thr Gly Leu Ala
            180                 185                 190

Asn Ala Lys Gln Lys Ser Phe Val Thr Gln His Ala Ala Phe Arg Tyr
        195                 200                 205

Leu Ala Leu Asp Tyr Gly Leu Lys Gln Val Pro Ile Ser Gly Leu Ser
    210                 215                 220
```

-continued

```
Pro Asp Ser Glu Pro Ser Ala Ala Arg Leu Ala Glu Leu Thr Lys Tyr
225                 230                 235                 240

Ile Lys Lys Asn Asn Ile Lys Tyr Ile Tyr Phe Glu Glu Asn Ala Ser
                245                 250                 255

Gln Ala Leu Ala Ser Thr Leu Ala Lys Glu Thr Gly Val Lys Leu Asp
            260                 265                 270

Val Leu Asn Pro Leu Glu Ser Leu Thr Glu Lys Gln Thr Lys Asp Gly
        275                 280                 285

Ala Asp Tyr Ile Ser Ile Met Lys Ser Asn Leu Lys Ala Leu Lys Lys
        290             295                 300

Thr Thr Asp Gln Ala Gly Ala Glu Ile Ser Ala Glu Lys Glu Lys Asn
305             310                 315                 320

Thr Lys Thr Val Gln Asn Gly Tyr Phe Glu Asp Ser Ala Val Lys Asp
                325                 330                 335

Arg Thr Leu Ser Asp Tyr Ala Gly Gln Trp Gln Ser Val Tyr Pro Tyr
            340                 345                 350

Leu Gln Asp Gly Thr Leu Asp Gln Val Phe Asp Tyr Lys Ala Lys Leu
        355                 360                 365

Ser Gly Lys Met Thr Ala Ala Glu Tyr Lys Ala Tyr Tyr Glu Lys Gly
        370             375                 380

Tyr Lys Thr Asp Val Ser His Ile Asn Ile Thr Asp Lys Thr Met Glu
385                 390                 395                 400

Phe Val Val Asn Gly Gln Lys Lys Phe Thr Tyr Lys Tyr Val Gly
                405                 410                 415

Lys His Thr Leu Thr Tyr Ser Lys Gly Asn Arg Gly Val Arg Phe Met
            420                 425                 430

Phe Glu Thr Thr Asp Lys Asp Ala Gly Lys Tyr Lys Tyr Val Gln Phe
        435                 440                 445

Ser Asp His Asn Ile Ala Pro Thr Lys Ala Ala His Phe His Ile Phe
450                 455                 460

Tyr Gly Gly Glu Asn Gln Glu Ala Leu Phe Asn Glu Leu Glu Asn Trp
465                 470                 475                 480

Pro Thr Tyr Tyr Pro Thr Lys Leu Ser Gly Gln Glu Ile Ala Gln Glu
                485                 490                 495

Met Leu Ala His
            500
```

COMPOSITIONS AND METHODS OF USE OF ORF-1358 FROM BETA-HEMOLYTIC STREPTOCOCCAL STRAINS

CROSS REFERENCE TO RELATED APPLICATIONS

The present application is a divisional application of U.S. application Ser. No. 12/487,831, filed on Jun. 19, 2009, which claims priority to Provisional Application No. 61/074,251, filed Jun. 20, 2008. The contents of these applications are hereby incorporated by reference in their entirety.

FIELD OF THE INVENTION

The invention relates to polynucleotides obtained from *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* and the polypeptides encoded by such polynucleotides.

BACKGROUND OF THE INVENTION

The beta-hemolytic *streptococcus* species are important pathogens responsible for numerous human diseases ranging from superficial infections to more severe illnesses. They include species from serological groups A, B, C and G. Group A *Streptococcus* bacteria (*Streptococcus pyogenes*) are accountable for most cases of illness and can result in non-invasive disease such as pharyngitis, scarlet fever, impetigo, cellulitis or erysipelas. Some *Streptococcus* strains can lead to more severe invasive infections such as toxic shock syndrome, necrotizing fasciitis and septicemia. Additionally, complications of surface infections can result in immune-mediated sequelae. Lancefield's Group B *streptococcus* (*Streptococcus agalactiae*) is the predominant cause of neonatal sepsis in neonates and can cause pneumonia in elderly patients. Streptococcal groups C and G were initially recognized as animal pathogens but in recent years have been shown to have a strong potential for human disease. Illness caused by Streptococcal groups C and G generally presents itself similarly as in Group A *streptococcus* but has not been shown to lead to immune-mediated sequelae. Group C and G streptococci are often present in patients with underlying health problems, are of importance for elderly patients and are dispersed among several streptococcal species.

SUMMARY OF THE INVENTION

The invention is based on the discovery of novel *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* polynucleotides corresponding to the *Streptococcus pyogenes* open reading frame 1358 (ORF1358). The invention encompasses the polypeptides encoded by such polynucleotides.

In one embodiment, the invention provides an isolated polypeptide that comprises at least a fragment of the amino acid sequence set forth in SEQ ID NO:31, which is a consensus sequence of the various novel ORF 1358 sequences obtained from *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharynges*. In some embodiments, the isolated polypeptide comprises an amino acid sequence set forth in SEQ ID NO:2, SEQ ID NO:4, SEQ ID NO:6, SEQ ID NO:8, SEQ ID NO:10, SEQ ID NO:12, SEQ ID NO:26, SEQ ID NO:28, SEQ ID NO:30, or SEQ ID NO:32, or a fragment thereof. In some embodiments, the isolated polypeptide comprises an amino acid sequence that is at least 97.5%, 98, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the isolated polypeptide has zinc-binding activity. In some embodiments the isolated polypeptide comprises an amino acid sequence that is at least 90%, 95%, 97.5%, 98, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32.

In one embodiment, the invention provides an isolated polynucleotide that encodes a polypeptide comprising an amino acid sequence set forth in SEQ ID NO:31, or a fragment thereof. In some embodiments, the isolated polynucleotide encodes a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or a fragment thereof. In some embodiments, the isolated polynucleotide comprises a nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, SEQ ID NO:31, or a fragment thereof. In some embodiments, the isolated polynucleotide encodes a polypeptide comprising an amino acid sequence that is at least 90%, 95%, 97.5%, 98, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the isolated polynucleotide comprises a nucleotide sequence that is at least 90%, 95%, or 99% identical to the polynucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31. In some embodiments, the isolated polynucleotide encodes a zinc binding polypeptide. In some embodiments, the polynucleotide is operably linked to a regulatory element. In some embodiments, the regulatory element comprises an inducible promoter and/or a constitutive promoter.

In one embodiment, the invention provides an antibody that specifically binds to at least a fragment of at least one *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 isolated polypeptide. In some embodiments, the antibody binds an isolated polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. The antibody may be a monoclonal antibody or a polyclonal antibody.

In one embodiment, the invention provides a kit comprising an ORF 1358 isolated polypeptide or a fragment thereof whose amino acid sequence is elucidated from *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyn-* ges. In some embodiments, the kit comprises an isolated polypeptide comprising an amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or a fragment thereof. In some embodiments, the kit comprises a polynucleotide vector expressing a polypeptide, or a fragment thereof, encoded by ORF 1358 of *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharynges*. In some embodiments, the kit comprises a polynucleotide vector expressing a polypeptide which comprises the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or a fragment thereof.

In one embodiment, the invention provides a polynucleotide vector expressing a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide. In some embodiments, the isolated polynucleotide vector expresses a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the polynucleotide vector comprises an isolated polynucleotide that encodes a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the polynucleotide vector comprises the nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31. In some embodiments, the polynucleotide vector comprises a polynucleotide that encodes a polypeptide comprising an amino acid sequence that is at least 90%, 95%, 97.5%, 98%, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the polynucleotide vector comprises an isolated polynucleotide that encodes a polypeptide with an amino acid sequence that is at least 90%, 95%, 97.5%, 98%, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the polynucleotide vector comprises an isolated polynucleotide that encodes a zinc binding polypeptide. In some embodiments, the polynucleotide vector comprises an isolated polynucleotide comprising a regulatory sequence operably linked to the isolated polynucleotide. In some embodiments, the polynucleotide vector comprises a regulatory element, which may be a constitutive promoter or an inducible promoter. In some embodiments, the polynucleotide vector is a plasmid, a viral vector, or an expression vector.

In one embodiment, the invention provides an immunogenic composition comprising an isolated *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF 1358 polypeptide. In some embodiments, the immunogenic composition comprises a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32.

In one embodiment, the invention provides an immunogenic composition comprising a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* isolated polynucleotide encoding an ORF1358 polypeptide. In some embodiments, the immunogenic composition comprises a polynucleotide comprising the nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31.

In one embodiment, the invention provides a method for inducing an immune response to beta hemolytic *Streptococcus* or beta hemolytic *Streptococcus* infection in a mammal comprising administering to the mammal an immunogenic composition comprising a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* isolated ORF1358 polypeptide.

In one embodiment, the invention provides an ex-vivo host cell expressing an isolated polypeptide encoded by *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358. In some embodiments, the host cell expresses a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the host cell comprises a polynucleotide vector comprising an isolated polynucleotide that encodes a polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32 In some embodiments, the host cell comprises a polynucleotide vector comprising the nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31. In some embodiments, the host cell comprises a polynucleotide vector comprising a polynucleotide that encodes a polypeptide comprising an amino acid sequence that is at least 90%, 95%, 97.5%, 98%, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the host cell comprises a polynucleotide vector comprising an isolated polynucleotide encoding a polypeptide with an amino acid sequence that is at least 90%, 95%, 97.5%, 98%, or 99% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the host cell comprises a polynucleotide vector comprising an isolated polynucleotide encoding a zinc binding polypeptide. In some embodiments, the host cell comprises a polynucleotide vector comprising an isolated polynucleotide comprising a regulatory sequence operably linked to the isolated polynucleotide. In some embodiments, the host cell comprises a polynucleotide vector comprising a regulatory element, which may be a constitutive promoter or an inducible promoter. In some embodiments, the host cell comprises a polynucleotide vector that is a plasmid, a viral vector, or an expression vector. In some embodiments the host cell is selected from a bacterium, a mammalian cell, an insect cell, or a yeast cell.

In one embodiment, the invention provides a kit comprising a polynucleotide or polypeptide comprising a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polynucleotide or polypeptide.

In one embodiment, the invention provides a method for treating a beta hemolytic *Streptococcus* infection in a mammal comprising administering a therapeutically effective amount of an antibody that specifically binds to at least one isolated polypeptide comprising a polypeptide encoded by *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358. In some embodiments, the method uses an antibody that binds an isolated polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:26, SEQ ID NO:28, SEQ ID NO:30, Or SEQ ID NO:32. The antibody used in the method may be a monoclonal antibody or a polyclonal antibody. In some embodiments, the beta hemolytic *Streptococcus* infection is treated in a human.

In one embodiment, the invention provides the use of an isolated polypeptide comprising a polypeptide encoded by *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF 1358 in the manufacture of a medicament useful in the prophylactic treatment of a beta hemolytic *Streptococcus* infection in a mammal. In some embodiments, the medicament is useful in a prophylactic treatment in a human.

In one embodiment, the invention provides a medicament useful in the prophylactic treatment of a beta hemolytic *Streptococcus* infection in a mammal. In some embodiments, the medicament uses an isolated *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* polynucleotide comprising an ORF1358 polypeptide. In some embodiments, the medicament uses an isolated polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. In some embodiments, the medicament uses an isolated *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* polynucleotide comprising an ORF1358 polynucleotide. In some embodiments, the medicament uses an isolated polynucleotide comprising the nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31. In some embodiments, the medicament uses a polynucleotide vector comprising a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polynucleotide. In some embodiments, the medicament uses an antibody that specifically binds to at least one isolated polypeptide comprising a polypeptide encoded by *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358. In some embodiments, the medicament uses an antibody that specifically binds an isolated polypeptide comprising the amino acid sequence set forth in SEQ ID NO:2, SEQ ID NO:4, SEQ ID NO:6, SEQ ID NO:8, SEQ ID NO:10, SEQ ID NO:12, SEQ ID NO:26, SEQ ID NO:28, SEQ ID NO:30, or SEQ ID NO:32. The medicament may use a monoclonal or a polyclonal antibody. In some embodiments, the mammal that the medicament is used in is a human.

BRIEF DESCRIPTION OF THE SEQUENCE LISTING

SEQ ID NO:1 is the nucleotide sequence of orf 1358 in a *Streptococcus dysgalactiae* subsp. *equisimilis*.

SEQ ID NO:2 is the amino acid sequence encoded by orf 1358 in a *Streptococcus dysgalactiae* subsp. *equisimilis* of SEQ ID NO:1.

SEQ ID NO:3 is the nucleotide sequence of orf 1358 in a *Streptococcus intermedius*.

SEQ ID NO:4 is the amino acid sequence encoded by orf 1358 in a *Streptococcus intermedius* of SEQ ID NO:3.

SEQ ID NO:5 is the nucleotide sequence of orf 1358 in a *Streptococcus constellatus* subsp. *constellatus*.

SEQ ID NO:6 is the amino acid sequence encoded by orf 1358 in a *Streptococcus constellatus* subsp. *constellatus* of SEQ ID NO:5.

SEQ ID NO:7 is the nucleotide sequence of orf 1358 in a *Streptococcus anginosus*.

SEQ ID NO:8 is the amino acid sequence encoded by orf 1358 in *Streptococcus anginosus* of SEQ ID NO:7.

SEQ ID NO:9 is the nucleotide sequence of orf 1358 in a *Streptococcus dysgalactiae* subsp. *equisimilis*.

SEQ ID NO:10 is the amino acid sequence encoded by orf 1358 in a *Streptococcus dysgalactiae* subsp. *equisimilis* of SEQ ID NO:9.

SEQ ID NO:11 is the nucleotide sequence of orf 1358 in *Streptococcus constellatus* subsp *pharyngis*.

SEQ ID NO:12 is the amino acid sequence encoded by orf 1358 in *Streptococcus constellatus* subsp. *pharyngis* of SEQ ID NO:11.

SEQ ID NO:13 is the consensus amino acid sequence obtained by aligning the polypeptide sequences set forth in SEQ ID NOs: 2, 4, 6, 8, 10, and 12.

SEQ ID NO:14 is the nucleotide sequence of primer D1358 F1.

SEQ ID NO:15 is the nucleotide sequence of primer D1358 F3.

SEQ ID NO:16 is the nucleotide sequence of primer D1358 F5.

SEQ ID NO:17 is the nucleotide sequence of primer D1358 R2.

SEQ ID NO:18 is the nucleotide sequence of primer D1358 R3.

SEQ ID NO:19 is the nucleotide sequence of primer D1358 R5.

SEQ ID NO:20 is the nucleotide sequence of primer 1358 F.

SEQ ID NO:21 is the nucleotide sequence of primer 1358 R.

SEQ ID NO:22 is the amino acid sequence of the *Streptococcus pyogenes* high-affinity zinc uptake system protein znuA precursor having NCBI gi 50902983.

SEQ ID NO:23 is the amino acid sequence of the *Streptococcus agalactiae* 2603V/R zinc binding adhesion lipoprotein having NCBI gi 22536713.

SEQ ID NO:24 is the amino acid sequence of the polypeptide encoded by a *Streptococcus agalactiae* oRF1358.

SEQ ID NO:25 is the nucleotide sequence of orf 1358 in a *Streptococcus dysgalactiae* subsp. *equisimilis*.

SEQ ID NO:26 is the amino acid sequence encoded by orf 1358 in a *Streptococcus dysgalactiae* subsp. *equisimilis* of SEQ ID NO:25.

SEQ ID NO:27 is the nucleotide sequence of orf 1358 in a *Streptococcus dysgalactiae* subsp. *equisimilis*.

SEQ ID NO:28 is the amino acid sequence encoded by orf 1358 in a in a *Streptococcus dysgalactiae* subsp. *equisimilis* of SEQ ID NO:27.

SEQ ID NO:29 is the nucleotide sequence of orf 1358 in a *Streptococcus anginosus*.

SEQ ID NO:30 is the amino acid sequence encoded by orf 1358 in a *Streptococcus anginosus* of SEQ ID NO:29.

SEQ ID NO:31 is the nucleotide sequence of orf 1358 in a *Streptococcus constellatus* subsp. *constellatus*.

SEQ ID NO:32 is the amino acid sequence encoded by orf 1358 in a *Streptococcus constellatus* subsp. *constellatus* of SEQ ID NO:31.

DETAILED DESCRIPTION

The invention describes novel polynucleotides obtained from *Streptococcus dysgalactiae* subsp. *equisimilis*, *Streptococcus intermedius*, *Streptococcus constellatus* subsp. *constellatus*, *Streptococcus anginosus*, and *Streptococcus constellatus* subsp. *pharyngis* (Streptococcal C+G) strains corresponding to *Streptococcus pyogenes* open reading frame 1358 (ORF1358). Polynucleotide and amino acid sequences for ORF 1358 are provided in published International patent application number WO 02/083859. The novel ORF1358 polynucleotides encode novel polypeptides. These polynucleotides and polypeptides may be used in immunogenic compositions to induce an immune response to beta hemolytic *streptococcus* or beta hemolytic *streptococcus* infection in a mammal.

The terms "polynucleotide", and "nucleic acid"/"nucleic acid fragment" are used interchangeably herein. These terms encompass nucleotides connected by phosphodiester linkages. A "polynucleotide" may be a ribonucleic acid (RNA) or deoxyribonucleic acid (DNA) polymer that is single- or double-stranded, that optionally contains synthetic, non-natural or altered nucleotide bases. A polynucleotide in the form of a polymer of DNA may comprise one or more segments of cDNA, genomic DNA, synthetic DNA, or mixtures thereof. Nucleotide bases are indicated hereinafter by a single letter code: adenine (A), guanine (G), thymine (T), cytosine (C), inosine (I) and uracil (U).

A "protein" or "polypeptide" is a chain of amino acids arranged in a specific order determined by the coding sequence in a polynucleotide encoding the polypeptide.

The term "Isolated" means altered "by the hand of man" from the natural state. If a composition or substance occurs in nature, in order for it to be considered "Isolated" it must have been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed hereinafter. Isolated polynucleotides or isolated polypeptides may be purified from a cell in which they naturally occur. Conventional nucleic acid and polypeptide purification methods known to skilled artisans may be used to obtain isolated polynucleotides or polypeptides disclosed herein.

The term "operably linked" refers to the association of nucleic acid sequences on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The ORF1358 polynucleotides and ORF1358 polypeptides described herein may be obtained using standard cloning and screening techniques. The *Streptococcus dysgalactiae* subsp. *equisimilis*, *Streptococcus intermedius*, *Streptococcus constellatus* subsp. *constellatus*, *Streptococcus anginosus*, and *Streptococcus constellatus* subsp. *pharyngis* ORF1358 polynucleotides may be obtained, for example, from genomic DNA, from a cDNA library derived from mRNA, from a genomic DNA library, or can be synthesized using well known and commercially available techniques, such as e.g. by PCR from a cDNA library or via RT-PCR (reverse transcription-polymerase chain reaction).

The term "recombinant" means, for example, that a polynucleotide is made by an artificial combination of two otherwise separated polynucleotide segments, e.g., by chemical synthesis or by the manipulation of isolated polynucleotides using genetic engineering techniques. A "recombinant DNA construct" comprises any of the isolated polynucleotides of the present invention operably linked to at least one regulatory element.

In one embodiment, the invention provides an isolated polypeptide that comprises the amino acid sequence set forth in SEQ ID NO:13. The amino acid sequence set forth in SEQ ID NO:13 is the consensus sequence obtained after aligning the amino acid sequences encoded by the *Streptococcus dysgalactiae* subsp. *equisimilis*, *Streptococcus intermedius*, *Streptococcus constellatus* subsp. *constellatus*, *Streptococcus anginosus*, and *Streptococcus constellatus* subsp. *pharyngis* polynucleotide sequences ORF1358 and set forth in SEQ ID NO:2, SEQ ID NO:4, SEQ ID NO:6, SEQ ID NO:8, SEQ ID NO:10, SEQ ID NO:12, SEQ ID NO:26, SEQ ID NO:28, SEQ ID NO:30, and SEQ ID NO:32.

In one embodiment, the invention provides isolated polynucleotides encoding polypeptides comprising SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or fragments thereof. Encompassed herein are polynucleotides that differ from the polynucleotide sequences shown in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31 due to degeneracy of the genetic code. These polynucleotides encode polypeptides comprising the same function as the polypeptide encoded by *Streptococcus pyogenes* ORF1358. The polypeptides may comprise zinc binding activity.

Orthologues and allelic variants of the *Streptococcus dysgalactiae* subsp. *equisimilis*, *Streptococcus intermedius*, *Streptococcus constellatus* subsp. *constellatus*, *Streptococcus anginosus*, and *Streptococcus constellatus* subsp. *pharyngis* ORF1358 polynucleotides can readily be identified using methods well known in the art. Allelic variants and orthologues of the ORF1358 polynucleotides can comprise a nucleotide sequence that is typically at least about 90-95% or more identical to any one or more of the nucleotide sequence shown in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31, or a fragments thereof. The allelic variants and orthologues of ORF1358 polynucleotides can encode a polypeptide that comprises an amino acid sequence that is at least 90%, 95%, or 97.5% identical to the amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32. Such polynucleotides can readily be identified as being able to hybridize under stringent conditions, to at least a fragment from any one or more of the polynucleotides having the nucleotide sequences set forth in SEQ ID NO:1, SEQ ID NO:3, SEQ ID NO:5, SEQ ID NO:7, SEQ ID NO:9, or SEQ ID NO:11, or a fragment thereof.

Moreover, the allelic variants and orthologues of ORF1358 polynucleotides can comprise only a fragment of the coding region of a *Streptococcus dysgalactiae* subsp. *equisimilis*, *Streptococcus intermedius*, *Streptococcus constellatus* subsp. *constellatus*, *Streptococcus anginosus*, and *Streptococcus constellatus* subsp. *pharyngis* ORF1358 polynucleotide or gene, such as a fragment of a polynucleotide set forth in SEQ ID NO:1, SEQ ID NO:3, SEQ ID NO:5, SEQ ID NO:7, SEQ ID NO:9, or SEQ ID NO:11, SEQ ID NO:25, SEQ ID NO:27, SEQ ID NO:29, or SEQ ID NO:31. In certain embodiments, such fragments encode immunogenic fragments.

It is well understood by one skilled in the art that many levels of sequence identity are useful in identifying related polynucleotides and polypeptides. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments were also performed using BLAST (Altschul SF, Madden TL, Schaffer A A, et al. Gapped BLAST and PSI-BLAST: a new generation of protein database search programs. *Nucleic Acids Research*. Sep. 1, 1997; 25(17):3389-3402).

The ORF1358 polynucleotides of the invention may be used, for example, for the production of recombinant polypeptides for inclusion in immunogenic compositions. For the production of recombinant polypeptides, the polynucleotide may include the coding sequence for the mature polypeptide, by itself, or the coding sequence for the mature polypeptide linked with other coding sequences, such as those encoding a leader or secretory sequence, a pre-, or pro- or prepro-protein sequence, or other fusion peptide portions. For example, a marker sequence which facilitates purification of the fused polypeptide can be linked to the coding sequence (see Gentz et al., Proc. Natl. Acad. Sci. USA, 86:821-824, 1989). The polynucleotide may also contain sequences 5' and/or 3' of the coding sequence, such as transcribed sequences, non-translated sequences, splicing signals, and polyadenylation signals.

In certain embodiments, the polynucleotide sequence information provided herein allows for the preparation of relatively short DNA (or RNA) oligonucleotide sequences having the ability to specifically hybridize to nucleotide sequences of the selected polynucleotides disclosed herein. The term "oligonucleotide" as used herein is defined as a molecule comprising two or more deoxyribonucleotides or ribonucleotides, usually more than three (3), and typically more than ten (10) and up to one hundred (100) or more (although preferably between twenty and thirty). The exact size will depend on many factors, which in turn depends on the ultimate function or use of the oligonucleotide. Thus, in some embodiments, nucleic acid probes of an appropriate length are prepared based on a selected nucleotide sequence, e.g., a sequence such as that shown in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31. The ability of such nucleic acid probes to specifically hybridize to a polynucleotide encoding a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide lends them particular utility in a variety of embodiments. In some embodiments, the probes can be used in a variety of assays for detecting the presence of complementary sequences in a given sample. These primers may be generated in any manner, including chemical synthesis, DNA replication, reverse transcription, or a combination thereof. The sequence of such primers is designed using a polynucleotide described herein for use in detecting, amplifying or mutating a defined segment of a polynucleotide that encodes a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide from prokaryotic cells using polymerase chain reaction (PCR) technology.

In some embodiments, the polynucleotides described herein may be used in combination with an appropriate label for detecting hybrid formation. A wide variety of appropriate labels are known in the art, including radioactive, enzymatic, or other ligands, such as avidin/biotin, which are capable of giving a detectable signal.

Polynucleotides which are identical or sufficiently identical to a nucleotide sequence contained in one of SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, SEQ ID NO:31, and SEQ ID NO:14 through SEQ ID NO:21, or a fragment thereof, may be used as hybridization probes for cDNA and genomic DNA, or as primers for a nucleic acid amplification (PCR) reaction, to isolate full-length cDNAs and genomic clones encoding polypeptides described herein and to isolate cDNA and genomic clones of other genes (including genes encoding homologs and orthologs from species other than *Streptococcus dysgalactiae*) that have a high sequence similarity to the polynucleotide sequences set forth in of SEQ ID NO:1, SEQ ID NO:3, SEQ ID NO:5, SEQ ID NO:7, SEQ ID NO:9, and SEQ ID NO:11, SEQ ID NO:25, SEQ ID NO:27, SEQ ID NO:29, or SEQ ID NO:31, or a fragment thereof. Typically these nucleotide sequences are from at least about 90% identical to at least about 99% identical to that of the reference polynucleotide sequence. The probes or primers will generally comprise at least 15 nucleotides, at least 30 nucleotides or at least 50 nucleotides.

There are several methods available and well known to those skilled in the art to obtain full-length cDNAs, or extend short cDNAs. For example those methods based on the method of Rapid Amplification of cDNA ends (RACE) (See Frohman et al., Proc. Natl. Acad. Sci. USA 85, 8998-9002, 1988). Modifications of this technique, exemplified by the Marathon™ technology (Clontech, Mountain View, Calif.) for example, have significantly simplified the search for longer cDNAs. In the Marathon™ technology, cDNAs are prepared from mRNA extracted from a chosen tissue and an "adaptor" sequence ligated onto each end. Nucleic acid amplification (PCR) is then carried out to amplify the "missing" 5' end of the cDNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

In one embodiment, the present invention provides isolated and purified *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides for use in immunogenic compositions. An ORF1358 polypeptide used in an immunogenic composition of the invention may be a recombinant polypeptide.

A *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide used in an immunogenic composition of the present invention encompasses a polypeptide that comprises an amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or a fragment thereof; functional and non-functional naturally occurring variants or biological equivalents of said polypeptides; recombinantly produced variants or biological equivalents of said polypeptides; orthologues, or allelic variants of said polypeptides.

Biological equivalents or variants of *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 include both functional and non-functional *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides. Functional biological equivalents or variants include naturally occurring amino acid sequence variants of a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide that maintains the ability to elicit an immunological or antigenic response in a subject. Functional variants typically contain conservative substitutions of one or more amino acids of one or more of SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32; or substitutions, deletions or insertions of non-critical residues in non-critical regions of the polypeptide.

In some embodiments, modifications and changes can be made in the structure of a polypeptide of the present invention and still obtain a molecule having the same antigenicity as the unchanged *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide. For example, certain amino acids can be substituted for other amino acids in a sequence without appreciable loss of antigenicity. Because it is the interactive capacity and nature of a polypeptide that defines that polypeptide's biological functional activity, certain amino acid sequence substitutions can be made in a polypeptide sequence (or its underlying DNA coding sequence) and nevertheless obtain a polypeptide with like properties.

In making changes to obtain orthologues or allelic variants, the hydropathic index of amino acids can be considered. The importance of the hydropathic amino acid index in conferring interactive biologic function on a polypeptide is generally understood in the art (Kyte and Doolittle, J Mol Biol, 157: p. 105-132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is generally accepted in the art that the relative hydropathic character of the amino acid residue determines the secondary and tertiary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In some embodiments, polynucleotides encoding ORF1358 polypeptide may comprise substituted amino acids whose hydropathic indices are within +/−2. In some embodiments, the hydrophobic indices are within +/−1, and some embodiments, the hydrophobic indices are within +/−0.5.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated hereinafter by reference, states that the greatest local average hydrophilicity of a polypeptide, as governed by the hydrophilicity of its adjacent amino acids, correlates with its immunogenicity and antigenicity.

A "variant," as the term is used herein is a polynucleotide or a polypeptide that differs from a reference polynucleotide or reference polypeptide respectively, while retaining at least one essential property. A typical variant of a polynucleotide differs in nucleotide sequence from a reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference polynucleotide, as discussed below. A typical variant of a polypeptide differs in amino acid sequence from a reference polypeptide. Generally, differences are limited so that the sequences of the reference polypeptide and the variant polypeptide are closely similar overall and, in many regions, identical. A variant polypeptide and its reference polypeptide may differ in amino acid sequence by one or more substitutions, additions, or deletions, in any combination. A substituted or inserted amino acid residue may or may not be one encoded by the genetic code. A variant of a polynucleotide or polypeptide may be naturally occurring such as an allelic variant, or it may be a variant that is not known to occur naturally. Non-naturally occurring variants of polynucleotides and polypeptides may be made by mutagenesis techniques or by direct synthesis.

For recombinant production of polypeptides, host cells are genetically engineered to incorporate expression systems, portions thereof, or polynucleotides of the invention. Polynucleotides comprising ORF1358 can be introduced into host cells e.g. by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd ed., Cold Spring Harbor Laboratory Press, Cold Spring Harbor, N.Y. (1989). These methods include e.g. calcium phosphate transfection, DEAE-dextran mediated transfection, transvection, microinjection, ultrasound, cationic lipid-mediated transfection, electroporation, transduction, scrape loading, ballistic introduction, and infection.

Representative examples of suitable host cells include bacterial cells (e.g., streptococci, staphylococci, *E. coli, Streptomyces* and *Bacillus subtilis* cells), yeast cells (e.g., *Pichia, Saccharomyces*), mammalian cells (e.g., vero, Chinese hamster ovary, chick embryo fibroblasts, BHK cells, human SW13 cells), and insect cells (e.g., Sf9, Sf21).

The recombinantly-produced polypeptides may be recovered and purified from recombinant cell cultures by well-known methods, including high performance liquid chromatography, ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography.

Any one or more systems may be used to express and produce the *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides in a heterologous cell system. Such systems include, among others, chromosomal, episomal and virus-derived systems. Vectors may be derived from bacterial plasmids, attenuated bacteria, bacteriophage, transposons, yeast episomes, insertion elements, yeast chromosomal elements, or viruses. Vectors may be obtained from viruses such as vaccinia and other poxviruses, sindbis, adenovirus, baculoviruses, papova viruses (such as SV40), fowl pox viruses, pseudorabies viruses, retroviruses, alphaviruses (such as Venezuelan equine encephalitis virus (U.S. Pat. No. 5,643,576)), nonsegmented negative-stranded RNA viruses such as vesicular stomatitis virus (U.S. Pat. No. 6,168,943). Vectors may also be derived from combinations thereof, such as those derived from plasmid and bacteriophage genetic elements, such as cosmids and phagemids. The expression systems should include control regions that regulate as well as engender expression, such as promoters and other regulatory elements (such as a polyadenylation signal). Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

In one embodiment, the present invention provides expression vectors expressing *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides for use in immunogenic compositions. The expression vectors comprise ORF1358 polynucleotides encoding polypeptides comprising an amino acid sequence set forth in SEQ ID NO:2, SEQ ID NO:4, SEQ ID NO:6, SEQ ID NO:8, SEQ ID NO:10, SEQ ID NO:12, SEQ ID NO:13, SEQ ID NO:26, SEQ ID NO:28, SEQ ID NO:30, Or SEQ ID NO:32, or a fragment thereof. Alternatively, the expression vectors comprise a polynucleotide comprising a nucleotide sequence set forth in SEQ ID NO:1, SEQ ID NO:3, SEQ ID NO:5, SEQ ID NO:7, SEQ ID NO:9, SEQ ID NO:11, SEQ ID NO:25, SEQ ID NO:27, SEQ ID NO:29, or SEQ ID NO:31, or a fragment thereof. In other embodiments, the expression vectors of the invention comprise a polynucleotide operatively linked to an enhancer-promoter. In still other embodiments, the expression vectors comprise a polynucleotide operatively linked to a prokaryotic promoter. Alternatively, the expression vectors comprise a polynucleotide operatively linked to an enhancer-promoter that is a eukaryotic promoter. The expression vectors further may comprise a polyadenylation signal that is positioned 3' of the carboxy-terminal amino acid and within a transcriptional unit of the encoded polypeptide.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". It is further recognized that since in most cases the exact boundaries of regulatory sequences have not been completely defined, nucleic acid fragments of different lengths may have identical promoter activity Commonly used promoters are derived from viruses such as polyoma, Adenovirus 2, cytomegalovirus, and Simian Virus 40. For other suitable expression systems for both prokaryotic and eukaryotic cells see chapters 16 and 17 of Sambrook et al., "Molecular Cloning: A Laboratory Manual" 2nd, ed, Cold Spring Harbor Laboratory, Cold Spring Harbor Laboratory Press, Cold Spring Harbor, N.Y., 1989, incorporated hereinafter by reference. In certain instances, the expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., Genes Dev, 1: p. 268-277, 1987), lymphoid-specific promoters (Calame and Eaton, Adv Immunol, 43: p. 235-275, 1988), in particular, promoters of T cell receptors (Winoto and Baltimore, EMBO J, 8: p. 729-733, 1989) and immunoglobulins (Banerji et al., Cell, 33: p. 729-740, 1983), (Queen and Baltimore, Cell, 33: p. 741-748, 1983), neuron-specific promoters (e.g., the neurofilament promoter; Byrne and Ruddle, PNAS, 86: p. 5473-5477, 1989), pancreas-specific promoters (Edlund et al., Science, 230: p. 912-916, 1985), and mammary gland-specific promoters (e.g., milk whey promoter; U.S. Pat. No. 4,873,316 and International Application EP 264,166). Developmentally-regulated promoters are also encompassed, for example the murine hox promoters (Kessel and Gruss, Science, 249: p. 374-379, 1990) and the α-fetoprotein promoter (Campes and Tilghman, Genes Dev, 3: p. 537-546, 1989).

Also provided herein are recombinant expression vectors comprising polynucleotides encoding at least a portion of a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptides cloned into the expression vector in an antisense orientation. That is, the DNA molecule is operatively linked to a regulatory sequence in a manner which allows for expression (by transcription of the DNA molecule) of an RNA molecule which is antisense to the *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide mRNA. Regulatory sequences operatively linked to a nucleic acid cloned in the antisense orientation can be chosen which direct the continuous expression of the antisense RNA molecule in a variety of cell types. For instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced.

The recombinant expression vectors described herein may be inserted into any suitable host cell. The terms "host cell" and "recombinant host cell" are used interchangeably herein. It is understood that such terms refer not only to the particular subject cell, but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide can be expressed in bacterial cells (such as *E. coli*), insect cells (such as Sf9, Sf21), yeast cells, or mammalian cells (such as Chinese hamster ovary cells (CHO), VERO, chick embryo fibroblasts, BHK cells or COS cells). Other suitable host cells are known to those skilled in the art.

Vector DNA is introduced into prokaryotic or eukaryotic cells via conventional transformation, infection or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, ultrasound or electroporation. Suitable methods for transforming or transfecting host cells can be found, for example, in Sambrook, et al. ("Molecular Cloning: A Laboratory Manual" 2nd, ed, Cold Spring Harbor Laboratory, Cold Spring Harbor Laboratory Press, Cold Spring Harbor, N.Y., 1989), and other laboratory manuals.

A host cell described herein, such as a prokaryotic or a eukaryotic host cell in culture, is used to produce (i.e., express) a *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide. Accordingly, also described herein are methods for producing a polypeptide using such host cells. In one embodiment, the method comprises culturing the host cell (into which a recombinant expression vector encoding an ORF1358 polypeptide has been introduced) in a suitable medium until the polypeptide is produced. In another embodiment, the method further comprises isolating the ORF1358 polypeptide from the medium or the host cell.

Expression of polypeptides in prokaryotes is most often carried out in *E. coli* with vectors containing constitutive or inducible promoters directing the expression of either fusion or non-fusion proteins. Constitutive promoters include, for example, lambda PL, spc ribosomal and beta-lactamase. Inducible promoters include, for example, arabinose, lac, tac and maltose binding protein. Fusion vectors add a number of amino acids to a protein encoded therein, usually to the amino terminus of the recombinant protein. Such fusion vectors typically serve three purposes: to increase expression of recombinant protein; to increase the solubility of the recombinant protein; and to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. The invention also provides vectors (e.g., expression vectors, sequencing vectors, cloning vectors) which comprise at least one polynucleotide of the invention, host cells which are genetically engineered with vectors of the invention, and production of polypeptides of the invention by recombinant techniques. Cell-free translation systems can also be employed to produce such proteins using RNAs derived from the DNA constructs of the invention.

Expression vectors useful to express *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptides are viral vectors, such as lentiviruses, retroviruses, herpes viruses, adenoviruses, adeno-associated viruses, vaccinia virus, baculovirus, and other recombinant viruses with desirable cellular tropism. Thus, a gene encoding a functional or mutant protein or polypeptide, or fragment thereof can be introduced in vivo, ex vivo, or in vitro using a viral vector or through direct introduction of DNA. Expression in targeted tissues can be effected by targeting the transgenic vector to specific cells, such as with a viral vector or a receptor ligand, or by using a tissue-specific promoter, or both. Targeted gene delivery is described in PCT Publication Number WO 95/28494.

Viral vectors commonly used for in vivo or ex vivo targeting and therapy procedures are DNA-based vectors and retroviral vectors. Methods for constructing and using viral vectors are known in the art (e.g., Miller and Rosman, BioTechniques, 1992, 7:980-990). Preferably, the viral vectors are replication-defective, that is, they are unable to replicate autonomously in the target cell. Preferably, the replication defective virus is a minimal virus, i.e., it retains only the sequences of its genome, which are necessary for encapsulating the genome to produce viral particles.

DNA viral vectors include an attenuated or defective DNA virus, such as, for example, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Thus, a specific tissue can be specifically targeted. Examples of particular vectors include, but are not limited to, a defective herpes virus 1 (HSV1) vector (Kaplitt et al., Molec. Cell. Neurosci., 1991, 2:320-330), defective herpes virus vector lacking a glycoprotein L gene, or other defective herpes virus vectors (PCT Publication Numbers WO 94/21807 and WO 92/05263); an attenuated adenovirus vector, such as the vector described by Stratford-Perricaudet et al. (J. Clin. Invest., 1992, 90:626-630; see also La Salle et al., Science, 1993, 259:988-990); and a defective adeno-associated virus vector (Samulski et al., J. Virol., 1987, 61:3096-3101; Samulski et al., J. Virol., 1989, 63:3822-3828; Lebkowski et al., Mol. Cell. Biol., 1988, 8:3988-3996).

The polypeptides of the invention, including those comprising the amino acid sequences set forth in SEQ ID NO:2, SEQ ID NO:4, SEQ ID NO:6, SEQ ID NO:8, SEQ ID NO:10, SEQ ID NO:12, or SEQ ID NO:13, their fragments, and analogs thereof, or cells expressing them, can also be used as immunogens to produce antibodies immunospecific for the polypeptides of the invention. The invention includes antibodies immunospecific for *streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides, the use of such antibodies to detect the presence of, or measure the quantity or concentration of *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides in a cell, a cell or tissue extract, or a biological fluid, or for treatment of *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* infection.

The antibodies of the invention include polyclonal antibodies, monoclonal antibodies, chimeric antibodies, and anti-idiotypic antibodies. Polyclonal antibodies are heterogeneous populations of antibody molecules derived from the sera of animals immunized with an antigen. Monoclonal antibodies are a substantially homogeneous population of antibodies to specific antigens. In general, antibodies can be made, for example, using traditional hybridoma techniques (Kohler and Milstein Nature, 256: 495-499, 1975), recombinant DNA methods (U.S. Pat. No. 4,816,567), or phage display using antibody libraries (Clackson et al. Nature 352: 624-628, 1991; Marks et al. J. Mol. Biol. 222: 581-597, 1991). For additional antibody production techniques, see Antibodies: A Laboratory Manual, eds. Harlow and Lane, Cold Spring Harbor Laboratory, 1988. The present invention is not limited to any particular source, method of production, or other special characteristics of an antibody.

Intact antibodies are immunoglobulins (Ig), and they typically are tetrameric glycpsylated proteins composed of two light chains (~25 kDa each) and two heavy chains (~50 kDa each). Light chains are classified into two isotypes (A and K), and heavy chains are classified into five isotypes (A, D, E, G, and M). Some heavy chain isotypes are further divided into isotype subclasses, e.g., $IgG_1$, $IgG_2$, $IgG_3$, and $IgG_4$.

The domain and three dimensional structures of different antibodies are known in the art (Harlow and Lane, supra). In brief, the light chain is composed of a constant domain ($C_L$) and an N-terminal variable domain ($V_L$). The heavy chain is composed of three or four constant domains ($C_H$), a hinge region, and a N-terminal variable domain ($V_H$). The $C_H$ adjacent to the $V_H$ domain is designated $C_{H1}$. The $V_H$ and $V_L$ domains contain four regions of conserved sequence called framework (FR) regions (FR1, FR2, FR3, and FR4), which form a scaffold for three regions of hypervariable sequence called complementarity determining regions (CDR). The CDRs (CDR1, CDR2, and CDR3) contain most of the antibody amino acids that specifically recognize and bind antigen. Heavy chain CDRs are denoted H1, H2, and H3, while light chain CDRs are denoted L1, L2, and L3.

The Fab fragment (Fragment antigen-binding) consists of $V_H$—$C_{H1}$ and $V_L$—$C_L$ domains covalently linked by a disulfide bond between the constant regions. The $F_v$ fragment is smaller and consists of $V_H$ and $V_L$ domains non-covalently linked. To overcome the tendency of non-covalently domains to dissociate, a single chain $F_v$ fragment ($scF_v$) can be constructed. The $scF_v$ contains a flexible polypeptide that links the (1) C-terminus of $V_H$ to the N-terminus of $V_L$, or the (2) C-terminus of $V_L$ to the N-terminus of $V_H$. A 15-mer $(Gly_4Ser)_3$ peptide may be used as a linker, but other linkers are known in the art.

Antibody diversity is created by use of multiple germline genes encoding variable regions and a variety of somatic events. The somatic events include recombination of variable gene segments and diversity (D) and joining (J) gene segments to make a complete $V_H$ region and the recombination of variable and joining gene segments to make a complete $V_L$ region. CDR3 (H3) is the greatest source of molecular diversity within an antibody sequence. H3, for example, can be as short as two amino acid residues or greater than 26. The smallest antigen-binding fragment is the Fv, which consists of the $V_H$ and the $V_L$ domains.

Anti-ORF1358 polypeptide antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Antibody isotype such as $IgG_1$, $IgG_2$, $IgG_3$ or $IgG_4$ is determined by the $CH_2$ and $CH_3$ domains. Isotypes may be switched by changing these domains without affecting antigen binding. Constant regions are known in the art (see, for example, Kabat et al., Sequences of Proteins of Immunological Interest, No. 91-3242, National Institutes of Health Publications, Bethesda, Md., 1991).

Chimeric antibodies are molecules, different portions of which are derived from different animal species, such as those having variable region derived from a murine monoclonal antibody and a human immunoglobulin constant region. Chimeric antibodies and methods for their production are known in the art (Cabilly et al., Proc. Natl. Acad. Sci. USA 81:3273-3277, 1984; Morrison et al., Proc. Natl. Acad. Sci. USA 81:6851-6855, 1984; Boulianne et al., Nature 312:643-646, 1984; Cabilly et al., European Patent Application No. 125023 (published Nov. 14, 1984); Taniguchi et al., European Patent Application No. 171496 (published Feb. 19, 1985); Morrison et al., European Patent Application No. 173494 (published Mar. 5, 1986); Neuberger et al., PCT Application No. WO 86/01533 (published Mar. 13, 1986); Kudo et al., European Patent Application No. 184187 (published Jun. 11, 1986); Morrison et al., European Patent Application No. 173494 (published Mar. 5, 1986); Sahagan et al., J. Immunol. 137: 1066-1074, 1986; Robinson et al., PCT/US86/02269 (published May 7, 1987); Liu et al., Proc. Natl. Acad. Sci. USA 84:3439-3443, 1987; Sun et al., Proc. Natl. Acad. Sci. USA 84:214-218, 1987; Better et al., Science 240:1041-1043, 1988).

An anti-idiotypic (anti-Id) antibody is an antibody that recognizes unique determinants generally associated with the antigen-binding site of an antibody. An anti-Id antibody is prepared by immunizing an animal of the same species and genetic type (e.g., mouse strain) as the source of the monoclonal antibody with the monoclonal antibody to which an anti-Id is being prepared. The immunized animal will recognize and respond to the idiotypic determinants of the immunizing antibody by producing an antibody to these isotypic determinants (the anti-Id antibody).

Accordingly, monoclonal antibodies generated against the polypeptides of the present invention may be used to induce anti-Id antibodies in suitable animals. Spleen cells from such immunized animals can be used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the final mAb specific for a R-PTPase epitope. The anti-Id antibodies thus have their idiotypic epitopes, or "idiotopes" structurally similar to the epitope being evaluated, such as *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* polypeptides encoded by ORF1358.

The term "antibody" is also meant to include both intact molecules as well as fragments such as Fab, which are capable of binding antigen. Fab fragments lack the Fc fragment of intact antibody, clear more rapidly from the circulation, and may have less non-specific tissue binding than an intact antibody (Wahl et al., J. Nucl. Med. 24:316-325, 1983). It will be appreciated that Fab and other fragments of the antibodies useful in the present invention may be used for the detection and quantitation of *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* polypeptides according to the methods for intact antibody molecules.

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The antibodies may be used in a variety of ways, e.g., for confirmation that a protein is expressed, or to confirm where a protein is expressed. Labeled antibody (e.g., fluorescent labeling for FACS) can be incubated with intact bacteria and the presence of the label on the bacterial surface confirms the location of the protein.

Other suitable methods of producing or isolating antibodies that specifically bind to a Group C or Group G streptococcal ORF1358 polypeptide epitope can be used. In some embodiments, the recombinant antibody is selected from a peptide or protein display library such as e.g. a bacteriophage, ribosome, oligonucleotide, RNA and cDNA display libraries (EP368,684; PCT/GB91/01134; PCT/GB92/01755; PCT/GB92/002240; PCT/GB92/00883; PCT/GB93/00605; PCT/GB94/01422; PCT/GB94/02662; PCT/GB97/01835; WO90/14443; WO90/14424; WO90/14430; PCT/US94/1234; WO92/18619; WO96/07754; EP614,989; WO95/16027; WO88/06630; WO90/3809; U.S. Pat. No. 4,704,692; PCT/US91/02989; WO89/06283; EP371,998; EP550,400; EP229,046; and PCT/US91/07149.) In other embodiments, the recombinant antibody is selected from a library of stochastically generated peptides or proteins (U.S. Pat. Nos. 5,723,323; 5,763,192; 5,814,476; 5,817,483; 5,824,514; 5,976,862; WO 86/05803; and EP 590,689.) In yet other embodiments, the recombinant antibody is produced in a transgenic animal that is capable of producing a repertoire of human antibodies (Nguyen et al., Microbiol. Immunol. 41:901-907, 1997; Sandhu et al., Crit. Rev. Biotechnol. 16:95-118, 1996; and Eren et al., Immunol. 93:154-161, 1998.) Other techniques for producing recombinant antibodies include e.g. single cell antibody producing technologies such as the selected lymphocyte antibody method ("SLAM") (U.S. Pat. No. 5,627,052), gel microdroplet and flow cytometry methods (Powell et al., Biotechnol. 8:333-337, 1990), and B-cell selection (Steenbakkers et al., Molec. Biol. Reports 19:125-134, 1994). These same methods can also be deployed to improve the affinity and/or avidity of an anti-Group C or Group G streptococcal PPI antibody to its specific binding target.

The present invention provides immunogenic compositions comprising one or more *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* polypeptides encoded by ORF1358. In certain embodiments, the immunogenic compositions comprise one or more *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* polypeptides comprising an amino acid residue sequence that is at least 97.5%, 98%, 99%, or 100% identical to SEQ ID NOs: 2, 4, 6, 8, 10, 12, 26, 28, 30, and 32, and one or more physiologically acceptable carriers.

In other embodiments, the immunogenic compositions of the invention comprise polynucleotides that encode the *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptides, and one or more physiologically acceptable carriers. In some embodiments, the immunogenic compositions comprise polynucleotides having a nucleotide sequence that is at least 90%, 95%, 99%, or 100% identical to one or more of SEQ ID NOs: 1, 3, 5, 7, 9, 11, 25, 27, 29, or 31.

The term "immunogenic composition" as used herein refers to any type of biological agent in an administratable form capable of stimulating an immune response in an animal (which includes human) inoculated with the immunogenic composition. An immune response may include induction of antibodies and/or induction of a T-cell response. Herein, the term "protection," when used in reference to an immunogenic composition, refers to the amelioration (either partial or complete) of any of the symptoms associated with the disease or condition in question. Thus, protection of animals from *Streptococcus* or infection by a *Streptococcus* species such as *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* by the present immunogenic compositions generally results in a diminishing of bacterial growth and/or one or more of the clinical symptoms associated with infection by *Streptococcus* species, including arthritis, endocarditis, meningitis, polyserositis, bronchopneumonia, meningitis, permanent hearing loss, and septic shock.

The methods disclosed herein may include inducing an immune response against one or more pathogens that include a species of *Streptococcus* (e.g., *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharynges*). For example, the methods may include inducing polyclonal antibodies against one or more pathogens that include a species of *Streptococcus* that may include *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharynges*. In some embodiments, the methods include administering to a subject (any vertebrate, including human patients and other mammals) a composition that includes an isolated *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptide or polynucleotide.

Various tests are used to assess the in vitro immunogenicity of the polypeptides of the invention. For example, an in vitro opsonic assay is conducted by incubating together a mixture of *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* cells, heat inactivated serum containing specific antibodies to the polypeptide in question, and an exogenous complement source. Opsonophagocytosis proceeds during incubation of freshly isolated polymorphonuclear cells (PMN's) and the antibody/complement/Streptococcus dysgalactiae subsp. *equisimilis*, *Streptococcus intermedius*, *Streptococcus constellatus* subsp. *constellatus*, *Streptococcus anginosus*, or *Streptococcus constellatus* subsp. *pharyngis* cell mixture. Bacterial cells that are coated with antibody and complement are killed upon opsonophagocytosis. Colony forming units (cfu) of surviving bacteria that escape from opsonophagocytosis are determined by plating the assay mixture. Titers are reported as the reciprocal of the highest dilution that gives 50% bacterial killing, as determined by comparison to assay controls. Specimens that demonstrate less than 50% killing at the lowest serum dilution tested (1:8), are reported as having an OPA (opsonophagocytosis antibody) titer of 4. The highest dilution tested is 1:2560. Samples with ≧50% killing at the highest dilution are repeated, beginning with a higher initial dilution. The method described above is a modification of Gray's method (Gray, Conjugate Vaccines Supplement, p. 694-697,1990). A test serum control, which contains test serum plus bacterial cells and heat inactivated complement, is included for each individual serum. This control is used to assess whether the presence of antibiotics or other serum components are capable of killing the bacterial strain directly (i.e. in the absence of complement or PMN's). A human serum with known opsonic titer is used as a positive human serum control. The opsonic antibody titer for each unknown serum is calculated as the reciprocal of the initial dilution of serum giving 50% cfu reduction compared to the control without serum.

A whole cell ELISA assay is also used to assess in vitro immunogenicity and surface exposure of the polypeptide antigen, wherein the bacterial strain of interest is coated onto a plate, such as a 96 well plate, and test sera from an immunized animal is reacted with the bacterial cells. If any antibody, specific for the test polypeptide antigen, is reactive with a surface exposed epitope of the polypeptide antigen, it can be detected by standard methods known to one skilled in the art.

Any polypeptide demonstrating the desired in vitro activity may then be tested in an in vivo animal challenge model. In certain embodiments, immunogenic compositions are used in the immunization of an animal (e.g., a mouse) by methods and routes of immunization known to those of skill in the art (e.g., intranasal, parenteral, intramuscular, oral, rectal, vaginal, transdermal, intraperitoneal, intravenous, subcutaneous, etc.). Following immunization of the animal with a particular *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* immunogenic composition, the animal is challenged with the same or other streptococcal species and assayed for resistance to the same or other *Streptococcus* spp. infection.

The *Streptococcus dysgalactiae* subsp. *equisimilis*, *Streptococcus intermedius*, *Streptococcus constellatus* subsp. *constellatus*, *Streptococcus anginosus*, or *Streptococcus constellatus* subsp. *pharyngis* ORF1358 polypeptides and polynucleotides are incorporated into immunogenic compositions suitable for administration to a subject, e.g., a human. Such compositions typically comprise the nucleic acid molecule or protein, together with a pharmaceutically acceptable carrier. As used hereinafter the language "pharmaceutically acceptable carrier" is intended to include any and all solvents, dispersion media, coatings, antibacterial and antifungal agents, isotonic and absorption delaying agents, excipients and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

An immunogenic composition of the invention is formulated to be compatible with its intended route of administration. Examples of routes of administration include parenteral (e.g., intramuscular, intravenous, intradermal, subcutaneous, intraperitoneal), transmucosal (e.g., oral, rectal, intranasal, vaginal, respiratory) and transdermal (topical). Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and the like. In many cases, isotonic agents are included, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide or antibody thereto) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems.

Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation (Mountain View, Calif.) and Nova Pharmaceuticals, Inc. (Baltimore, Md.). Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Combination immunogenic compositions are provided by combining one or more of the polypeptides of the invention with one or more known streptococcal polysaccharides or polysaccharide-protein conjugates.

The protein component of the carbohydrate-protein conjugates is known as a "carrier protein". The term "carrier proteins", includes those proteins that are non-toxic, non-reactogenic and obtainable in sufficient amount and purity. Carrier proteins are amenable to standard conjugation procedures. For example, $CRM_{197}$ can be used as the carrier protein. $CRM_{197}$, (Wyeth, Sanford, N.C.) is a non-toxic variant (toxoid) of diphtheria toxin isolated from cultures of *Corynebacterium diphtheria* strain C7 (β197) grown in casamino acids and yeast extract-based medium. $CRM_{197}$ is purified through ultra-filtration, ammonium sulfate precipitation, and ion-exchange chromatography. Other diphtheria toxoids are also suitable for use as carrier proteins.

Other suitable carrier proteins include inactivated bacterial toxins such as tetanus toxoid, pertussis toxoid, cholera toxoid (as described e.g. in PCT Publication No. WO/2004/083251), *E. coli* LT, *E. coli* ST, and exotoxin A from *Pseudomonas aeruginosa*. Bacterial outer membrane proteins such as outer membrane complex c (OMPC), porins, transferrin binding proteins, pneumolysis, pneumococcal surface protein A (PspA), pneumococcal adhesin protein (PsaA), or *Haemophilus influenzae* protein D, can also be used. Other proteins, such as ovalbumin, keyhole limpet hemocyanin (KLH), bovine serum albumin (BSA) or purified protein derivative of tuberculin (PPD) can also be used as carrier proteins.

Immunogenic compositions comprising *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polynucleotides are delivered to the recipient by a variety of vectors and expression systems. Such systems include, among others, chromosomal, episomal and virus-derived systems as mentioned above.

An immunogenic composition of the present invention is typically administered parenterally in unit dosage formulations containing standard, well-known nontoxic physiologically acceptable carriers, adjuvants, and vehicles as desired.

A pharmaceutically acceptable vehicle is understood to designate a compound or a combination of compounds entering into a pharmaceutical or immunogenic composition which does not cause side effects and which makes it possible, for example, to facilitate the administration of the active compound, to increase its life and/or its efficacy in the body, to increase its solubility in solution or alternatively to enhance its preservation. These pharmaceutically acceptable vehicles are well known and will be adapted by persons skilled in the art according to the nature and the mode of administration of the active compound chosen.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Carriers include neutral saline solutions buffered with phosphate, lactate, Tris, and the like. When administering viral vectors, one purifies the vector sufficiently to render it essentially free of undesirable contaminants, such as defective interfering adenovirus particles or endotoxins and other pyrogens such that it does not cause any untoward reactions in the individual receiving the vector construct. In some embodiments, the means of purifying the vector involves the use of buoyant density gradients, such as cesium chloride gradient centrifugation.

A carrier can also be a liposome. Means for using liposomes as delivery vehicles are well known in the art (see, e.g. the review by Schwendener RA, Adv. Exp. Med. Biol. 620: 117-128, 2007)

The immunogenic compositions of this invention also comprise a polynucleotide sequence of this invention operably linked to a regulatory sequence that controls gene expression. The polynucleotide sequence of interest is engineered into an expression vector, such as a plasmid, under the control of regulatory elements that will promote expression of the DNA, that is, promoter and/or enhancer elements. In some embodiments, the human cytomegalovirus immediate-early promoter/enhancer is used (U.S. Pat. No. 5,168,062). The promoter may be cell-specific and permit substantial transcription of the polynucleotide only in predetermined cells.

The polynucleotides of the invention are introduced directly into the host either as "naked" DNA (U.S. Pat. No. 5,580,859) or formulated in compositions with facilitating agents, such as bupivacaine and other local anesthetics (U.S. Pat. No. 5,593,972) and cationic polyamines (U.S. Pat. No. 6,127,170). In this polynucleotide immunization procedure, the polypeptides of the invention are expressed on a transient basis in vivo; no genetic material is inserted or integrated into the chromosomes of the host. This procedure is to be distinguished from gene therapy, where the goal is to insert or integrate the genetic material of interest into the chromosome. An assay is used to confirm that the polynucleotides administered by immunization do not give rise to a transformed phenotype in the host (e.g., U.S. Pat. No. 6,168,918).

Immunogenic compositions as described herein also comprise, in certain embodiments, one or more adjuvants. An adjuvant is a substance that enhances the immune response when administered together with an immunogen or antigen. A number of cytokines or lymphokines have been shown to have immune modulating activity, and thus are useful as adjuvants, including, but not limited to, the interleukins 1-$\alpha$, 1-$\beta$, 2, 4, 5, 6, 7, 8, 10, 12 (see, e.g., U.S. Pat. No. 5,723,127), 13, 14, 15, 16, 17 and 18 (and its mutant forms); the interferons-$\alpha$, $\beta$ and $\gamma$; granulocyte-macrophage colony stimulating factor (GM-CSF) (see, e.g., U.S. Pat. No. 5,078,996 and ATCC Accession Number 39900); macrophage colony stimulating factor (M-CSF); granulocyte colony stimulating factor (G-CSF); and the tumor necrosis factors $\alpha$ and $\beta$. Still other adjuvants that are useful with the immunogenic compositions described herein include chemokines, including without limitation, MCP-1, MIP-1$\alpha$, MIP-1$\beta$, and RANTES; adhesion molecules, such as a selectin, e.g., L-selectin, P-selectin and E-selectin; mucin-like molecules, e.g., CD34, GlyCAM-1 and MadCAM-1; a member of the integrin family such as LFA-1, VLA-1, Mac-1 and p150.95; a member of the immunoglobulin superfamily such as PECAM, ICAMs, e.g., ICAM-1, ICAM-2 and ICAM-3, CD2 and LFA-3; co-stimulatory molecules such as CD40 and CD40L; growth factors including vascular growth factor, nerve growth factor, fibroblast growth factor, epidermal growth factor, B7.2, PDGF, BL-1, and vascular endothelial growth factor; receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6; and Caspase (ICE).

Suitable adjuvants used to enhance an immune response further include, without limitation, MPL™ (3-O-deacylated monophosphoryl lipid A, Corixa, Hamilton, Mont.), which is described in U.S. Pat. No. 4,912,094. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918. One such AGP is 2-[(R)-3-Tetradecanoyloxytetradecanoylamino]ethyl 2-Deoxy-4-O-phosphono-3-O-[(R)-3-tetradecanoyoxytetradecanoyl]-2-[(R)-3-tetradecanoyloxytetradecanoyl-amino]-b-D-glucopyranoside, which is also known as 529 (formerly known as RC529). This 529 adjuvant is formulated as an aqueous form (AF) or as a stable emulsion (SE).

Still other adjuvants include muramyl peptides, such as N-acetyl-muramyl-L-threonyl-D-isoglutamine (thr-MDP), N-acetyl-normuramyl-L-alanine-2-(1'-2' dipalmitoyl-sn-glycero-3-hydroxyphosphoryloxy)-ethylamine (MTP-PE); oil-in-water emulsions, such as MF59 (U.S. Pat. No. 6,299,884) (containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton, Mass.)), and SAF (containing 10% Squalene, 0.4% Tween 80, 5% pluronic-blocked polymer L121, and thr-MDP, either microfluidized into a submicron emulsion or vortexed to generate a larger particle size emulsion); incomplete Freund's adjuvant (IFA); aluminum salts (alum), such as aluminum hydroxide, aluminum phosphate, aluminum sulfate; Amphigen; Avridine; L121/squalene; D-lactide-polylactide/glycoside; pluronic polyols; killed *Bordetella*; saponins, such as Stimulon™ QS-21 (Antigenics, Framingham, Mass.), described in U.S. Pat. No. 5,057,540, ISCOMATRIX (CSL Limited, Parkville, Australia), described in U.S. Pat. No. 5,254,339, and immunostimulating complexes (ISCOMS); *Mycobacterium tuberculosis*; bacterial lipopolysaccharides; synthetic polynucleotides such as oligonucleotides containing a CpG motif (e.g., U.S. Pat. No. 6,207,646); IC-31 (Intercell AG, Vienna, Austria), described in European Patent Nos. 1,296,713 and 1,326,634; a pertussis toxin (PT) or mutant thereof, a cholera toxin or mutant thereof (e.g., U.S. Pat. Nos. 7,285,281, 7,332,174, 7,361,355 and 7,384,640); or an *E. coli* heat-labile toxin (LT) or mutant thereof, particularly LT-K63, LT-R72 (e.g., U.S. Pat. Nos. 6,149,919, 7,115,730 and 7,291,588).

The present invention is directed inter alia to treatment of streptococcal infection by administration of therapeutic immunological reagents such as humanized monoclonal antibodies recognizing specific epitopes within a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide to a subject under conditions that generate a beneficial therapeutic response in the subject. "Immunological reagents" include e.g. antibodies, humanized antibodies, antibody fragments, peptides comprising antigen binding elements or CDRs, and the like. "Beneficial therapeutic responses" include e.g. induction of phagocytosis or opsonization of beta-hemolytic streptococci. The invention is also directed to use of the disclosed immunological reagents in the manufacture of a medicament for the treatment or prevention of a beta-hemolytic streptococcal infection.

In one aspect, the invention provides methods of preventing or treating disease associated with beta-hemolytic streptococcal infection in a patient. Some methods of the invention entail administering to a patient an effective dosage of an antibody that specifically binds to a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 epitope. Such methods are particularly useful for preventing or treating beta-hemolytic streptococcal disease in subjects. "Subjects" include any vertebrate animal, such as companion animals, farm animals, mammals, and human patients. Exemplary methods include administering an effective dosage of an antibody or antigen binding peptide that binds to a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide. Some embodiments include administering an effective dosage of an antibody or other peptide comprising an antigen recognition site or CDR that specifically binds to an epitope within a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide, such as e.g. a polypeptide comprising an amino acid sequence of any one or more of SEQ ID NOs: 2, 4, 6, 8, 10, 12, 13, 26, 28, 30, or 32.

In yet another aspect, the invention features administering antibodies or other antigen binding peptides that bind to a *Streptococcus dysgalactiae* subsp. *equisimilis, Streptococcus intermedius, Streptococcus constellatus* subsp. *constellatus, Streptococcus anginosus*, or *Streptococcus constellatus* subsp. *pharyngis* ORF1358 polypeptide in the subject and induce a clearing response against a beta-hemolytic *streptococcus*. For example, such a clearing response can be effected by Fc receptor mediated phagocytosis.

Therapeutic immunological reagents of the invention are typically substantially pure from undesired contaminants. This means that an immunological reagent is typically at least about 50% w/w (weight/weight) purity, as well as being substantially free from interfering proteins and contaminants. In some embodiments, the immunological reagents are at least about 80% w/w purity. In other embodiments, the immunological reagents are at least 90 or about 95% w/w purity. However, using conventional protein purification techniques, homogeneous peptides of at least 99% w/w purity can be obtained.

The methods can be used on both asymptomatic subjects and those currently showing symptoms of disease. The antibodies used in such methods can be human, humanized, chimeric or nonhuman antibodies, or fragments thereof (e.g., antigen binding fragments, peptides comprising epitope binding regions or CDRs) and can be monoclonal or polyclonal, as described herein.

In another aspect, the invention features administering an antibody with a pharmaceutical carrier as a pharmaceutical composition. Alternatively, the antibody can be administered to a subject by administering a polynucleotide encoding at least one antibody chain. The polynucleotide is expressed to produce the antibody chain in the patient. Optionally, the polynucleotide encodes heavy and light chains of the antibody. The polynucleotide is expressed to produce the heavy and light chains in the patient. In exemplary embodiments, the patient is monitored for level of administered antibody in the blood of the patient.

Subjects amenable to treatment include individuals at risk of disease but not showing symptoms, as well as patients presently showing symptoms. Therefore, the present immunogenic compositions and therapeutic antibodies can be administered prophylactically to the general population. In asymptomatic subjects, treatment can begin at any age. Treatment can be monitored by assaying antibody levels over time. If the immune response or antibody level falls, a booster dosage is indicated.

In prophylactic applications, immunogenic compositions or medicaments are administered to a subject susceptible to, or otherwise at risk of, beta-hemolytic streptococcal infection in an amount sufficient to eliminate or reduce the risk, lessen the severity, or delay the outset of the disease, including biochemical, histological and/or behavioral symptoms of disease associated with the infection, its complications and intermediate pathological phenotypes presenting during development of the disease. In therapeutic applications, compositions or medicaments are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease.

An amount adequate to accomplish therapeutic or prophylactic treatment is defined as a therapeutically- or prophylactically-effective dose. In both prophylactic and therapeutic regimes, immunological reagents are usually administered in several dosages until a sufficient immune response has been achieved. The term "immune response" or "immunological response" includes the development of a humoral (antibody mediated) and/or a cellular (mediated by antigen-specific T cells or their secretion products) response directed against an antigen in a recipient subject. Such a response can be an active response, i.e., induced by administration of immunogen (supra), or a passive response, i.e., induced by administration of immunoglobulin or antibody or primed T-cells. Typically, the immune response is monitored and repeated dosages are given if the immune response starts to wane.

Effective doses of the compositions of the present invention, for the treatment of beta-hemolytic streptococcal infection vary depending upon many different factors, including means of administration, target site, physiological state of the patient, whether the patient is human or another animal, other medications administered, and whether treatment is prophylactic or therapeutic. Usually, the subject is a human but non-human mammals including transgenic mammals can also be treated. Treatment dosages may need to be titrated to optimize safety and efficacy.

For passive immunization with an antibody, the dosage ranges from about 0.0001 to 100 mg/kg, and more usually 0.01 to 5 mg/kg (e.g., 0.02 mg/kg, 0.1 mg/kg, 0.15 mg/kg, 0.2 mg/kg, 0.25 mg/kg, 0.5 mg/kg, 0.75 mg/kg, 1 mg/kg, 2 mg/kg, etc.), of the host body weight. For example dosages can be about 1 mg/kg body weight or about 10 mg/kg body weight or within the range of 1 to 10 mg/kg. Doses intermediate in the above ranges are also intended to be within the scope of the invention. Subjects can be administered such doses daily, on alternative days, weekly, monthly, every two months, every three months, or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months. Exemplary dosage schedules include 1 to 10 mg/kg or 15 mg/kg on consecutive days, 30 mg/kg on alternate days or 60 mg/kg weekly. In some methods, two or more monoclonal antibodies with different binding specificities are administered simultaneously, in which case the dosage of each antibody administered falls within the ranges indicated.

Antibody is usually administered on multiple occasions. Intervals between single dosages can be weekly, monthly or yearly. Intervals can also be irregular as indicated by measuring blood levels of antibody to *Streptococcus dysgalactiae* subsp. *equisimilis, Streptococcus intermedius, Streptococcus constellatus* subsp. *constellatus, Streptococcus anginosus,* or *Streptococcus constellatus* subsp. *pharyngis* ORF1358 polypeptide in the patient. In some methods, dosage is adjusted to achieve a plasma antibody concentration of 1 to 1000 μg/ml and in some methods 25 to 300 μg/ml. Alternatively, antibody can be administered as a sustained release formulation, in which case less frequent administration is required. Dosage and frequency vary depending on the half-life of the antibody in the patient. In general, humanized antibodies show the longest half-life, followed by chimeric antibodies and nonhuman antibodies The dosage and frequency of administration can vary depending on whether the treatment is prophylactic or therapeutic. In prophylactic applications, compositions containing the present antibodies or a cocktail thereof are administered to a patient not already in the disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time.

In therapeutic applications, a relatively high dosage (e.g., from about 1 to 200 mg of antibody per dose, with dosages of from 5 to 25 mg being more commonly used) at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding antibodies range from about 10 ng to 1 g, 100 ng to 100 mg, 1 μg to 10 mg, or 30 to 300 μg DNA per patient. Doses for infectious viral vectors vary from 10 to 100, or more, virions per dose.

Therapeutic immunological reagents can be administered by parenteral, topical, intravenous, oral, subcutaneous, intraarterial, intracranial, intraperitoneal, intranasal or intramuscular means for prophylactic and/or therapeutic treatment. The most typical routes of administration of an immunogenic agent are intravenous infusion or subcutaneous administration, although other routes can be equally effective. The next most common route is intramuscular injection. This type of injection is most typically performed in the arm or leg muscles. In some methods, immunological reagents are injected directly into a particular tissue where deposits have accumulated, for example intracranial injection. Intramuscular injection or intravenous infusion are preferred for administration of antibody. In some methods, antibodies are administered as a sustained release composition or device, such as a microinfusor device (e.g. Medipad™ device; see Meehan et al., Journal of Controlled Release, 46:107-119, 1997.)

As alluded to above, immune responses against beta-hemolytic streptococcal infection can be formed in vivo (or ex vivo) by administration of nucleic acids encoding antibodies and their component chains used for passive immunization. Such nucleic acids can be DNA or RNA. A nucleic acid segment encoding an immunological reagent is typically linked to regulatory elements, such as a promoter and enhancer, that allow expression of the DNA segment in the intended target cells of a patient. For expression in blood cells, as is desirable for induction of an immune response, promoter and enhancer elements from light or heavy chain immunoglobulin genes or the CMV major intermediate early promoter and enhancer are suitable to direct expression. The linked regulatory elements and coding sequences are often cloned into a vector. For administration of double-chain antibodies, the two chains can be cloned in the same or separate vectors.

A number of viral vector systems are available including retroviral systems (see, e.g., Lawrie and Tumin, Cur. Opin. Genet. Develop. 3:102 109 (1993)); adenoviral vectors (see, e.g., Bett et al., J. Virol. 67:5911 (1993)); adeno-associated virus vectors (see, e.g., Zhou et al., J. Exp. Med. 179:1867 (1994)), viral vectors from the pox family including vaccinia virus and the avian pox viruses, viral vectors from the alpha virus genus such as those derived from Sindbis and Semliki Forest Viruses (see, e.g., Dubensky et al., J. Virol. 70:508, 1996), Venezuelan equine encephalitis virus (see Johnston et al., U.S. Pat. No. 5,643,576) and rhabdoviruses, such as vesicular stomatitis virus (see Rose, U.S. Pat. No. 6,168,943) and papillomaviruses (Ohe et al., Human Gene Therapy 6:325, 1995; Woo et al., PCT publication No. WO 94/12629 and Xiao and Brandsma, Nucleic Acids. Res. 24: 2630-2622, 1996).

DNA encoding an antibody or antibody fragment comprising a CDR, or a vector containing the same, can be packaged into liposomes. Suitable lipids and related analogs are described by Eppstein et al., U.S. Pat. No. 5,208,036, Feigner et al., U.S. Pat. No. 5,264,618, Rose, U.S. Pat. No. 5,279,833, and Epand et al., U.S. Pat. No. 5,283,185. Vectors and DNA encoding an immunogen can also be adsorbed to or associated with particulate carriers, examples of which include polymethyl methacrylate polymers and polylactides and poly (lactide-co-glycolides), see, e.g., McGee et al., J. Microencapsul. 14(2):197-210, 1997.

Polynucleotide vectors or naked polynucleotides (e.g., DNA) can be delivered in vivo by administration to an individual patient, typically by systemic administration (e.g., intravenous, intraperitoneal, nasal, gastric, intradermal, intramuscular, subdermal, or intracranial infusion) or topical application (see e.g., Anderson et al., U.S. Pat. No. 5,399,346). The term "naked polynucleotide" refers to a polynucleotide which is not administered together with a transfection facilitating agent. Naked polynucleotides are sometimes cloned in a plasmid vector. Plasmid vectors can further include transfection facilitating agents such as bupivacaine (Weiner et al., U.S. Pat. No. 5,593,972). DNA can also be administered using a gene gun. See Xiao and Brandsma, supra. The DNA encoding an antibody (or fragment comprising a CDR) is precipitated onto the surface of microscopic metal beads. The microprojectiles are accelerated with a shock wave or expanding helium gas, and penetrate tissues to a depth of several cell layers. For example, The ACCEL™ Gene Delivery Device, i.e., a DNA gun, manufactured by Agricetus, Inc. Middleton Wis. is suitable for use in the practice of this invention. Alternatively, naked DNA can pass through skin into the blood stream simply by spotting the DNA onto skin with chemical or mechanical irritation (see Howell et al., PCT Publication No. WO 95/05853).

In another embodiment, vectors encoding immunological reagents can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Immunological reagents of the invention can optionally be administered in combination with other agents that are at least partly effective in treatment of beta-hemolyic streptococcal disease. Immunological reagents of the invention can also be administered in combination with other agents that enhance access of the therapeutic immunological reagent to a target cell or tissue, for example, liposomes and the like. Coadministering such agents can decrease the dosage of a therapeutic immunological reagent (e.g., therapeutic antibody or antibody chain) needed to achieve a desired effect.

Immunological reagents of the invention are often administered as pharmaceutical compositions comprising an active therapeutic agent, i.e., and a variety of other pharmaceutically acceptable components. See Remington's Pharmaceutical Science (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, immunological reagents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation, which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, Science 249: 1527 (1990) and Hanes, Advanced Drug Delivery Reviews 28:97 (1997)). The immunological reagents of this invention can be administered in the form of a depot injection or implant preparation, which can be formulated in such a manner as to permit a sustained or pulsatile release of the active ingredient.

Additional formulations suitable for other modes of administration include oral, intranasal, and pulmonary formulations, suppositories, and transdermal applications. For suppositories, binders and carriers include, for example, polyalkylene glycols or triglycerides; such suppositories can be formed from mixtures containing the active ingredient in the range of 0.5% to 10%, preferably 1% to 2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10% to 95% of active ingredient, preferably 25% to 70%.

Alternatively, transdermal delivery can be achieved using a skin patch or using transferosomes (Paul et al., Eur. J. Immunol. 25:3521, 1995; Cevc et al., Biochem. Biophys. Acta 1368:201-215, 1998).

The invention also provides methods of monitoring treatment in a patient suffering from or susceptible to beta-hemolytic streptococcal infection, i.e., for monitoring a course of treatment being administered to a patient. The methods can be used to monitor both therapeutic treatment on symptomatic patients and prophylactic treatment on asymptomatic patients. In particular, the methods are useful for monitoring passive immunization (e.g., measuring level of administered antibody).

Some methods entail determining a baseline value, for example, of an antibody level or profile in a patient, before administering a dosage of immunological reagent, and comparing this with a value for the profile or level after treatment. A significant increase (i.e., greater than the typical margin of experimental error in repeat measurements of the same sample, expressed as one standard deviation from the mean of such measurements) in value of the level or profile signals a positive treatment outcome (i.e., that administration of the immunological reagent has achieved a desired response). If the value for immune response does not change significantly, or decreases, a negative treatment outcome is indicated. If the treatment is passive immunotherapy, the antibody level is expected to decrease over time with a characteristic half-life.

The tissue sample for analysis is typically blood, plasma, serum, mucous fluid or cerebrospinal fluid from the patient. The sample is analyzed, for example, for levels or titers of antibodies to streptococcal PPI. ELISA methods of detecting antibodies specific to streptococcal PPI are described in the Examples section. In some methods, the level or titer of an administered antibody is determined using a clearing assay, for example, in an in vitro phagocytosis assay (see, e.g., Jansen et al., Clin. Diagn. Lab. Immunol., 8(2): 245-250, 2001.)

The antibody profile following passive immunization typically shows an immediate peak in antibody concentration followed by an exponential decay. Without a further dosage, the decay approaches pretreatment levels within a period of days to months depending on the half-life of the antibody administered.

In some methods, a baseline measurement of antibody to streptococcal PPI in the patient is made before administration, a second measurement is made soon thereafter to determine the peak antibody level, and one or more further measurements are made at intervals to monitor decay of antibody levels. When the level of antibody has declined to baseline or a predetermined percentage of the peak less baseline (e.g., 50%, 25% or 10%), administration of a further dosage of antibody is administered. In some methods, peak or subsequent measured levels less background are compared with reference levels previously determined to constitute a beneficial prophylactic or therapeutic treatment regime in other patients. If the measured antibody level is significantly less than a reference level (e.g., less than the mean minus one standard deviation of the reference value in population of patients benefiting from treatment) administration of an additional dosage of antibody is indicated.

Additional methods include monitoring, over the course of treatment, any art-recognized physiologic symptom routinely relied on by researchers or physicians to diagnose or monitor streptococcal infections or associated diseases. For example, one can monitor symptoms of cellulitis, erysipelas, impetigo, necrotizing fasciitis, sore throat, red throat, chills, fever, headache, nausea, vomiting, rapid heartbeat, malaise, swollen tonsils. enlarged lymph nodes and/or rash.

The specification is most thoroughly understood in light of the teachings of the references cited within the specification, all of which are hereby incorporated by reference in their entirety. The embodiments within the specification provide an illustration of embodiments of the invention and should not be construed to limit the scope of the invention. The skilled artisan recognizes that many other embodiments are encompassed by the claimed invention and that it is intended that the specification and examples be considered as exemplary only, with a true scope and spirit of the invention being indicated by the following claims.

EXAMPLES

Example 1

Identification of ORF1358 in Streptococcal Strains

The DNA and protein sequences of Streptococcal candidate antigens have been identified in many of streptococcal genomes. However, limited sequence information exists on the Group C and G Streptococcal genomes. Currently, two animal-origin streptococcal genomes (Group C) are being sequenced by the Sanger Centre, *Streptococcus equi* and *Streptococcus zooepidemicus*. Data mining of the partially finished genomes using degenerate primers yielded DNA sequences of ORF1358.

Degenerate oligonucleotide probes were designed to identify ORF1358 in *Streptococcus dysgalactiae* subsp. *equisimilis* strain ATCC12394 and strain ATCC35666, *Streptococcus intermedius* strain ATCC27335, *Streptococcus constellatus* subsp. *constellatus* strain ATCC27823, *Streptococcus anginosus* strain ATCC33397, and *Streptococcus constellatus* subsp. *pharyngis* strain NTCT13122.

All known sequences containing ORF1358 were aligned using AlignX (Vector NTI) and regions of homology were used for degenerate primer construction. Primers were designed to have minimal degeneracy while maintaining a high melting temperature and low self dimerization potential. The nucleotide sequences of the primers are set forth in SEQ ID NOs:14 through 21.

Primers were analyzed using the website for Integrated DNA Technologies (Coraville, Iowa). Initial amplification studies were performed using genomic DNA preparations made to a *Streptococcus* C isolate ATCC12394 (*Streptococcus dysgalactiae* supsp. *equisimilis*). Partial gene sequences were obtained to the 5' and 3' of ORF1358. Forward and reverse primers were then designed based on these sequences and were subsequently used to amplify approximately 700-900 by of sequence from ORF1358 from different G and C strains. The primers based on ATCC12394 are set forth in SEQ ID NO:20 and 21.

Using methods familiar to those skilled in the art, genomic DNA was prepared from each of the strains mentioned above, and polynucleotide fragments corresponding to ORF1358 were amplified using the primers set forth in SEQ ID NO:14-21. The nucleotide sequences obtained for ORF1358 are set forth in SEQ ID NOs:1, 3, 5, 7, 9, 11, 25, 27, 29, and 31.

Translation of these polynucleotides resulted in the amino acid sequences of ORF1358 in these *Streptococcus* strains. The polynucleotide sequences are set forth in SEQ ID NOs:2, 4, 6, 8, 10, 12, 26, 28, 30, and 32.

The amino acid sequences in SEQ ID NOs:2, 4, 6, 8, 10, and 12 were aligned using Clustal W, and a consensus sequence generated and set forth in SEQ ID NO:13.

Table 1A depicts the pair distances obtained using ClustalW (slow/accurate, Gonnet) or percent identity obtained after aligning the ORF1358 amino acid sequences set forth in SEQ ID NOs: 2,4,6,8,10, and 12 with the ORF1358 amino acid sequences set forth in SEQ ID NOs:22, 23, and 24:

TABLE 1A

Streptococcal Percent Identities

|  | SEQ ID NO: 22 | SEQ ID NO: 23 | SEQ ID NO: 24 |
| --- | --- | --- | --- |
| SEQ ID NO: 2 | 96.6 | 72.9 | 87.1 |
| SEQ ID NO: 4 | 96.5 | 72.9 | 87.7 |
| SEQ ID NO: 6 | 96.9 | 73.6 | 87.0 |
| SEQ ID NO: 8 | 97.2 | 73.5 | 87.3 |
| SEQ ID NO: 10 | 97.0 | 73.5 | 87.1 |
| SEQ ID NO: 12 | 97.3 | 74.0 | 87.2 |

Table 1B depicts the pair distances or percent identity obtained using BLAST after aligning the ORF1358 amino acid sequences set forth in SEQ ID NOs:2,4,6,8,10,12, 26, 28, 30, and 32 with the ORF1358 amino acid sequences set forth in SEQ ID NOs:22 and 23:

TABLE 1B

Streptococcal Percent Identities

|  | SEQ ID NO: 22 | SEQ ID NO: 23 |
| --- | --- | --- |
| SEQ ID NO: 2 | 96 | 71 |
| SEQ ID NO: 4 | 96 | 71 |
| SEQ ID NO: 6 | 97 | 70 |
| SEQ ID NO: 8 | 97 | 70 |
| SEQ ID NO: 10 | 96 | 70 |
| SEQ ID NO: 12 | 97 | 71 |
| SEQ ID NO: 26 | 96 | 69 |
| SEQ ID NO: 28 | 96 | 70 |
| SEQ ID NO: 30 | 61 | 62 |
| SEQ ID NO: 32 | 61 | 61 |

Example 2

Antibodies to Group C/G Staphylococcal ORF 1358 Epitopes

The binding of antibodies to bacteria, a process known as opsonization, can lead to uptake and killing of the bacteria by phagocytic cells. Such antibodies, whether derived from bulk human or animal sources, or human or murine or chimeric monoclonal sources, and used alone or in combination, could be used in either prophylactic or therapeutic settings where BHS might be present in the bloodstream, such as neonatal sepsis or sepsis following surgery or leaking of an abscess.

Antibodies were raised in mice against recombinant group C/G staphylococcal zinc binding polypeptides encoded by ORF1358. In the course of screening those anti-beta-hemolytic-streptococcal antisera and monoclonal antibodies against various beta-hemolytic streptococcal (BHS) strains, it was noted that some antisera and antibodies are cross-reactive against many BHS strains, including members of *Streptococcus pyogenes* (Group A streptococci), *Streptococcus agalactiae* (Group B streptococci) and Group C and Group G streptococci (which include the streptococcal species *Streptococcus anginosus, Streptococcus constellatus, Streptococcus intermedius, Streptococcus dysgalactiae* sub. *Equisimilis* and *Streptococcus dysgalactiae* sub. *Dysgalactiae*) (See Table 1). Screening of the antibodies was performed using fluorescence activated cell sorting (FACS). Briefly, heat killed streptococci were incubated with a mouse anti-Group C and Group G ORF1358 streptococcal antibody on ice for 45 minutes, followed by two 10% FBS/PBS washes. The streptococci were then incubated with a goat anti-mouse-Alexa-488 antibody (Molecular Probes, Eugene, Oreg.) for 30 minutes on ice, followed by two 10% FBS/PBS washes. Cells were then resuspended in 10% FBS/PBS and run on a FACS machine (e.g. see DeMaster et al., Infect. Immun., 70(1): 350-359, 2002.) This cross-reactivity also means that Group C or Group G ORF1358 or the polypeptide encoded thereby may be used in an immunogenic composition to induce an immune response effective to protect against infection by Group A or Group B *Streptococcus*, as well as by Group C or Group G *Streptococcus*.

Table 2 depicts the cross reactivity of anti-sera and antibodies to the group c/g streptococcal polypeptide encoded by ORF1358. According to Table 2, the symbol "+" means that the signal obtained from the specific antibody to the antigen is at least three-fold higher than background; the symbol "+/−" means that the signal obtained from the specific antibody to the antigen is between two-fold and three-fold higher than background; and the sysmbol "−" means that the signal obtained from the specific antibody to the antigen is at or below background.

TABLE 2

ANTIBODY CROSS-REACTIVITY

| Strain | Species | Reactivity to anti-ORF 1358 |
| --- | --- | --- |
| GAR 1165 | *Streptococcus pyogenes* | + |
| GAR 1199 | *Streptococcus pyogenes* | + |
| GAR 1251 | *Streptococcus pyogenes* | + |
| GAR 1278 | *Streptococcus pyogenes* | + |
| GAR 1362 | *Streptococcus pyogenes* | + |
| GAR 1439 | *Streptococcus pyogenes* | + |
| GAR 1530 | *Streptococcus pyogenes* | + |
| GAR 1566 | *Streptococcus pyogenes* | + |
| GAR 1672 | *Streptococcus pyogenes* | + |
| GAR 1839 | *Streptococcus pyogenes* | + |
| GAR 1923 | *Streptococcus pyogenes* | + |
| GAR 2107 | *Streptococcus pyogenes* | + |
| GAR 2330 | *Streptococcus pyogenes* | + |
| GAR 2646 | *Streptococcus pyogenes* | + |
| GAR 2650 | *Streptococcus pyogenes* | + |
| GAR 2869 | *Streptococcus pyogenes* | + |
| GAR 3104 | *Streptococcus pyogenes* | + |
| GAR 3549 | *Streptococcus pyogenes* | + |
| GAR 3784 | *Streptococcus pyogenes* | + |
| GAR 4029 | *Streptococcus pyogenes* | + |
| GAR 4030 | *Streptococcus pyogenes* | + |
| GAR 4230 | *Streptococcus pyogenes* | + |
| GAR 4773 | *Streptococcus pyogenes* | + |
| GAR 4983 | *Streptococcus pyogenes* | + |
| GAR 4987 | *Streptococcus pyogenes* | + |
| GAR 5861 | *Streptococcus pyogenes* | + |
| GAR 5991 | *Streptococcus pyogenes* | + |
| GAR 6084 | *Streptococcus pyogenes* | + |
| GAR 7055 | *Streptococcus pyogenes* | + |
| GS20 | *Streptococcus pyogenes* | + |
| GS21 | *Streptococcus pyogenes* | + |
| GS22 | *Streptococcus pyogenes* | + |
| GS23 | *Streptococcus pyogenes* | + |
| GS24 | *Streptococcus pyogenes* | + |
| GS25 | *Streptococcus pyogenes* | + |
| GS26 | *Streptococcus pyogenes* | + |
| GS27 | *Streptococcus pyogenes* | + |
| GS28 | *Streptococcus pyogenes* | + |
| GS29 | *Streptococcus pyogenes* | + |
| GS30 | *Streptococcus pyogenes* | + |
| GS31 | *Streptococcus pyogenes* | +/− |
| GS32 | *Streptococcus pyogenes* | + |
| GS33 | *Streptococcus pyogenes* | + |
| GS34 | *Streptococcus pyogenes* | + |
| GS35 | *Streptococcus pyogenes* | + |
| GS36 | *Streptococcus pyogenes* | +/− |
| GS37 | *Streptococcus pyogenes* | + |
| GS38 | *Streptococcus pyogenes* | + |
| GS39 | *Streptococcus pyogenes* | + |

TABLE 2-continued

ANTIBODY CROSS-REACTIVITY

| Strain | Species | Reactivity to anti-ORF 1358 |
|---|---|---|
| GS40 | Streptococcus pyogenes | + |
| GS41 | Streptococcus pyogenes | + |
| GS42 | Streptococcus pyogenes | +/− |
| GS43 | Streptococcus pyogenes | + |
| GS44 | Streptococcus pyogenes | + |
| GS45 | Streptococcus pyogenes | + |
| GS46 | Streptococcus pyogenes | + |
| GS47 | Streptococcus pyogenes | +/− |
| GS48 | Streptococcus pyogenes | +/− |
| GS49 | Streptococcus pyogenes | + |
| GS50 | Streptococcus pyogenes | + |
| GS51 | Streptococcus pyogenes | + |
| GS52 | Streptococcus pyogenes | + |
| GS53 | Streptococcus pyogenes | + |
| GS54 | Streptococcus pyogenes | +/− |
| GS55 | Streptococcus pyogenes | + |
| GS56 | Streptococcus pyogenes | + |
| GS57 | Streptococcus pyogenes | + |
| GS58 | Streptococcus pyogenes | + |
| GS59 | Streptococcus pyogenes | + |
| GS60 | Streptococcus pyogenes | + |
| GS61 | Streptococcus pyogenes | + |
| GS62 | Streptococcus pyogenes | + |
| GS63 | Streptococcus pyogenes | + |
| GS64 | Streptococcus pyogenes | + |
| GS65 | Streptococcus pyogenes | + |
| GS66 | Streptococcus pyogenes | + |
| GAR 1 | Streptococcus agalactiae | + |
| GAR 1012 | Streptococcus agalactiae | − |
| GAR 1023 | Streptococcus agalactiae | − |
| GAR 1049 | Streptococcus agalactiae | − |
| GAR 10895 | Streptococcus agalactiae | − |
| GAR 1192 | Streptococcus agalactiae | +/− |
| GAR 127 | Streptococcus agalactiae | − |
| GAR 12790 | Streptococcus agalactiae | − |
| GAR 1305 | Streptococcus agalactiae | − |
| GAR 131 | Streptococcus agalactiae | − |
| GAR 1355 | Streptococcus agalactiae | − |
| GAR 1446 | Streptococcus agalactiae | − |
| GAR 1494 | Streptococcus agalactiae | − |
| GAR 154 | Streptococcus agalactiae | + |
| GAR 176 | Streptococcus agalactiae | − |
| GAR 18 | Streptococcus agalactiae | + |
| GAR 1844 | Streptococcus agalactiae | − |
| GAR 1931 | Streptococcus agalactiae | − |
| GAR 2369 | Streptococcus agalactiae | +/− |
| GAR 252 | Streptococcus agalactiae | − |
| GAR 2533 | Streptococcus agalactiae | − |
| GAR 2682 | Streptococcus agalactiae | − |
| GAR 2717 | Streptococcus agalactiae | − |
| GAR 2723 | Streptococcus agalactiae | − |
| GAR 2724 | Streptococcus agalactiae | − |
| GAR 2842 | Streptococcus agalactiae | − |
| GAR 287 | Streptococcus agalactiae | − |
| GAR 3003 | Streptococcus agalactiae | − |
| GAR 3751 | Streptococcus agalactiae | − |
| GAR 381 | Streptococcus agalactiae | − |
| GAR 3830 | Streptococcus agalactiae | − |
| GAR 4131 | Streptococcus agalactiae | − |
| GAR 4293 | Streptococcus agalactiae | +/− |
| GAR 4398 | Streptococcus agalactiae | − |
| GAR 462 | Streptococcus agalactiae | − |
| GAR 4837 | Streptococcus agalactiae | − |
| GAR 54 | Streptococcus agalactiae | − |
| GAR 562 | Streptococcus agalactiae | + |
| GAR 6016 | Streptococcus agalactiae | + |
| GAR 614 | Streptococcus agalactiae | +/− |
| GAR 63 | Streptococcus agalactiae | + |
| GAR 6332 | Streptococcus agalactiae | + |
| GAR 6387 | Streptococcus agalactiae | +/− |
| GAR 6505 | Streptococcus agalactiae | +/− |
| GAR 67 | Streptococcus agalactiae | − |
| GAR 864 | Streptococcus agalactiae | +/− |
| GAR 967 | Streptococcus agalactiae | − |
| GS19 | GGS | +/− |
| GS27 | GGS | +/− |
| ATCC 33397 | Streptococcus anginosus | +/− |
| ATCC 33397 | Streptococcus anginosus | − |
| GAR 10823 | Streptococcus anginosus | +/− |
| GAR 1272 | Streptococcus anginosus | − |
| GAR 1370 | Streptococcus anginosus | − |
| GAR 1425 | Streptococcus anginosus | +/− |
| GAR 1592 | Streptococcus anginosus | − |
| GAR 1595 | Streptococcus anginosus | − |
| GAR 2044 | Streptococcus anginosus | − |
| GAR 2523 | Streptococcus anginosus | − |
| GAR 2565 | Streptococcus anginosus | − |
| GAR 2697 | Streptococcus anginosus | +/− |
| GAR 2822 | Streptococcus anginosus | − |
| GAR 3091 | Streptococcus anginosus | − |
| GAR 3560 | Streptococcus anginosus | + |
| GAR 3576 | Streptococcus anginosus | +/− |
| GAR 3858 | Streptococcus anginosus | +/− |
| GAR 3938 | Streptococcus anginosus | − |
| GAR 4133 | Streptococcus anginosus | +/− |
| GAR 4158 | Streptococcus anginosus | + |
| GAR 4234 | Streptococcus anginosus | + |
| GAR 4426 | Streptococcus anginosus | + |
| GAR 4680 | Streptococcus anginosus | + |
| GAR 4834 | Streptococcus anginosus | +/− |
| GAR 4896 | Streptococcus anginosus | + |
| GAR 5093 | Streptococcus anginosus | + |
| GAR 5094 | Streptococcus anginosus | + |
| GAR 5675 | Streptococcus anginosus | − |
| GAR 5776 | Streptococcus anginosus | + |
| GAR 5831 | Streptococcus anginosus | +/− |
| GAR 6187 | Streptococcus anginosus | +/− |
| GAR 6590 | Streptococcus anginosus | +/− |
| GAR 7000 | Streptococcus anginosus | +/− |
| GAR 7023 | Streptococcus anginosus | − |
| GAR 7190 | Streptococcus anginosus | − |
| GAR 7214 | Streptococcus anginosus | +/− |
| GAR 7468 | Streptococcus anginosus | − |
| GAR 7818 | Streptococcus anginosus | + |
| GAR 8620 | Streptococcus anginosus | + |
| GAR 8693 | Streptococcus anginosus | − |
| GAR 8722 | Streptococcus anginosus | +/− |
| GAR 8736 | Streptococcus anginosus | − |
| GAR 8954 | Streptococcus anginosus | +/− |
| ATCC 27823 | Streptococcus constellatus | − |
| GAR 1235 | Streptococcus constellatus | − |
| GAR 1384 | Streptococcus constellatus | +/− |
| GAR 1811 | Streptococcus constellatus | + |
| GAR 2421 | Streptococcus constellatus | +/− |
| GAR 3145 | Streptococcus constellatus | − |
| GAR 3355 | Streptococcus constellatus | − |
| GAR 4048 | Streptococcus constellatus | +/− |
| GAR 4083 | Streptococcus constellatus | + |
| GAR 4861 | Streptococcus constellatus | + |
| GAR 4870 | Streptococcus constellatus | + |
| GAR 5757 | Streptococcus constellatus | +/− |
| GAR 6129 | Streptococcus constellatus | +/− |
| GAR 6147 | Streptococcus constellatus | − |
| GAR 6258 | Streptococcus constellatus | + |
| GAR 7224 | Streptococcus constellatus | + |
| GAR 7369 | Streptococcus constellatus | + |
| ATCC 12394 | Streptococcus dysgalactiae | +/− |
| ATCC 12394 | Streptococcus dysgalactiae | + |
| ATCC 40378 | Streptococcus dysgalactiae | − |
| ATCC 40378 | Streptococcus dysgalactiae | − |
| GAR 3868 | Streptococcus dysgalactiae | +/− |
| GAR 4272 | Streptococcus dysgalactiae | + |
| ATCC 35666 | Streptococcus dysgalactiae sub. Equisimilis | + |
| BAA-338 | Streptococcus dysgalactiae sub. Equisimilis | +/− |
| GAR 3015 | Streptococcus equisimilis | + |
| ATCC 27335 | Streptococcus intermedius | + |
| ATCC 27335 | Streptococcus intermedius | + |
| GAR 2407 | Streptococcus intermedius | − |

TABLE 2-continued

ANTIBODY CROSS-REACTIVITY

| Strain | Species | Reactivity to anti-ORF 1358 |
|---|---|---|
| GS28 | unk | + |
| GS67 | GGS/GCS | + |
| GS68 | GGS/GCS | +/− |
| GS69 | GGS/GCS | − |
| GS70 | GGS/GCS | +/− |
| GS71 | GGS/GCS | + |
| GS72 | GGS/GCS | + |
| GS73 | GGS/GCS | − |
| GS74 | GGS/GCS | − |
| GS75 | GGS/GCS | +/− |
| GS77 | GGS/GCS | + |
| GS78 | GGS/GCS | + |
| GS79 | GGS/GCS | +/− |
| GS80 | GGS/GCS | − |

TABLE 2-continued

ANTIBODY CROSS-REACTIVITY

| Strain | Species | Reactivity to anti-ORF 1358 |
|---|---|---|
| GS81 | GGS/GCS | +/− |
| GS82 | GGS/GCS | +/− |
| GS83 | GGS/GCS | + |
| GS84 | GGS/GCS | − |
| GS85 | GGS/GCS | − |
| GS86 | GGS/GCS | +/− |
| GS88 | GGS/GCS | + |
| GS89 | GGS/GCS | +/− |
| GS90 | GGS/GCS | +/− |
| GS91 | GGS/GCS | +/− |
| GS92 | GGS/GCS | + |
| GS93 | GGS/GCS | + |
| GS94 | GGS/GCS | + |

What is claimed:

1. An isolated polypeptide that comprises an amino acid sequence that is at least 95% identical to SEQ ID NO:32.

2. The isolated polypeptide of claim 1, wherein the polypeptide comprises an amino acid sequence that is at least 97% identical to SEQ ID NO:32.

3. An immunogenic composition comprising an isolated polypeptide that comprises:
   a) an amino acid sequence that is at least 95% identical to SEQ ID NO:32; or
   b) the amino acid sequence of SEQ ID NO:32.

4. A method for inducing an immune response to a beta hemolytic *Streptococcus* bacterium or to a beta hemolytic streptococcal infection in a patient comprising administering to the patient the immunogenic composition of claim 3.

5. The method of claim 4 wherein the beta hemolytic *Streptococcus* bacterium or the beta hemolytic streptococcal infection is from a Group A, Group B, Group C or Group G *streptococcus*.

6. A kit comprising an isolated polypeptide that comprises an amino acid sequence that is at least 95% identical to SEQ ID NO:32.

* * * * *